United States Patent
Yokoyama et al.

(10) Patent No.: US 11,618,777 B2
(45) Date of Patent: Apr. 4, 2023

(54) METHOD OF MANUFACTURING MEMBRANE PROTEIN AND UTILIZATION THEREOF

(71) Applicant: Shigeyuki Yokoyama, Tokyo (JP)

(72) Inventors: Shigeyuki Yokoyama, Saitama (JP); Takehiro Shinoda, Saitama (JP); Kaori Ito, Saitama (JP); Naoko Nomura, Saitama (JP); Yoshiko Katsura, Saitama (JP); Tomomi Someya, Saitama (JP); Mikako Shirouzu, Saitama (JP); Tetsuya Hori, Saitama (JP); Yoshihiro Nakamura, Saitama (JP); Hiroaki Tanabe, Saitama (JP)

(73) Assignee: Shigeyuki Yokoyama, Tokyo (JP)

( * ) Notice: Subject to any disclaimer, the term of this patent is extended or adjusted under 35 U.S.C. 154(b) by 950 days.

(21) Appl. No.: 16/327,193

(22) PCT Filed: Jul. 29, 2016

(86) PCT No.: PCT/JP2016/072444
§ 371 (c)(1),
(2) Date: Feb. 21, 2019

(87) PCT Pub. No.: WO2017/022696
PCT Pub. Date: Feb. 9, 2017

(65) Prior Publication Data
US 2019/0194286 A1  Jun. 27, 2019

(30) Foreign Application Priority Data
Jul. 31, 2015 (JP) .............................. JP2015-152932

(51) Int. Cl.
*C12P 21/02* (2006.01)
*C07K 14/705* (2006.01)
*C12N 15/09* (2006.01)
*C12N 9/64* (2006.01)

(52) U.S. Cl.
CPC .......... *C07K 14/705* (2013.01); *C12N 9/6478* (2013.01); *C12N 15/09* (2013.01); *C12P 21/02* (2013.01); *C12Y 304/23046* (2013.01)

(58) Field of Classification Search
CPC .................................................. C12N 9/2462
See application file for complete search history.

(56) References Cited

U.S. PATENT DOCUMENTS

| | | | |
|---|---|---|---|
| 5,264,341 A | 11/1993 | Maciak | |
| 5,270,181 A | 12/1993 | Mccoy | |
| 5,532,151 A | 7/1996 | Chantry | |
| 5,674,729 A | 10/1997 | Wimmer | |
| 5,800,984 A | 9/1998 | Vary | |
| 5,804,374 A | 9/1998 | Baltimore | |
| 5,869,286 A | 2/1999 | Yao | |
| 5,959,085 A | 9/1999 | Garrone | |
| 5,962,246 A | 10/1999 | Ladner | |
| 6,136,568 A | 10/2000 | Hiatt | |
| 6,303,337 B1 | 10/2001 | Rothschild | |
| 6,511,832 B1 | 1/2003 | Guarino | |
| 6,780,607 B2 | 8/2004 | Choi | |
| 7,045,593 B2* | 5/2006 | Tajima ................. | C07K 14/705 435/69.1 |
| 7,195,895 B2 | 3/2007 | Motoda | |
| 7,253,144 B2 | 8/2007 | Shirouzu | |
| 7,348,134 B2 | 3/2008 | Lingappa | |
| 2002/0025525 A1 | 2/2002 | Shuber | |
| 2002/0142387 A1 | 10/2002 | Seki | |
| 2003/0050453 A1 | 3/2003 | Sorge | |
| 2004/0121346 A1 | 6/2004 | Endo | |
| 2004/0137448 A1 | 7/2004 | Thornton | |
| 2004/0203091 A1 | 10/2004 | Tajima et al. | |
| 2005/0095705 A1 | 5/2005 | Kadan | |
| 2005/0244920 A1 | 11/2005 | Shirouzu | |

(Continued)

FOREIGN PATENT DOCUMENTS

| EP | 0469610 | 2/1992 |
|---|---|---|
| EP | 1143009 A1 | 10/2001 |

(Continued)

OTHER PUBLICATIONS

Kimura-Soyema et al, Cell-free membrane protein expression. Methods Mol Biol 2014; vol. 1118, p. 267-73 In: Cell-Free Protein Synthesis. Kirill Alexandrov and Wayne A. Johnston (eds.), First Online: Dec. 18, 2013.*

Vukoti, K. et al. Stabilization of functional recombinant cannabinoid receptor CB2 in detergent micelles and lipid bilayers. PLoS One, Oct. 2012, vol. 7, issue 10, e46290, pp. 1-19.

Windisch, D. et al. Hydrophobic Mismatch Drives the Interaction of E5 with the Transmembrane Segment of PDGF Receptor. Biophysical Journal, vol. 109, Aug. 2015, 737-749.

Ritchie, T.K. et al. "Reconstitution of Membrane Proteins in Phospholipid Bilayer Nanodiscs" Methods Enzymol. 2009; 464: 211-231.

(Continued)

*Primary Examiner* — Tekchand Saidha
(74) *Attorney, Agent, or Firm* — Casimir Jones, S.C.; Tanya A. Arenson

(57) ABSTRACT

In order to provide a membrane protein production method which does not require the step of solubilizing a membrane protein and which allows the membrane protein having an excellent quality to be obtained with a high yield, a method in accordance with an embodiment of the present invention includes: a step (a) of preparing a reaction solution for cell-free protein synthesis, the reaction solution containing (i) a template nucleic acid which encodes the membrane protein, (ii) a lipid, and (iii) a detergent which is contained at a concentration equal to or higher than a critical micelle concentration; and a step (b) of synthesizing the membrane protein while the concentration of the detergent in the reaction solution is maintained at a concentration equal to or higher than a critical micelle concentration.

2 Claims, 18 Drawing Sheets

Specification includes a Sequence Listing.

(56) References Cited

U.S. PATENT DOCUMENTS

| | | | |
|---|---|---|---|
| 2005/0255542 | A1 | 11/2005 | Shirouzu et al. |
| 2007/0117179 | A1 | 5/2007 | Kudlicki et al. |
| 2007/0281337 | A1 | 12/2007 | Imataka |
| 2008/0248565 | A1 | 10/2008 | Katzen et al. |
| 2009/0161828 | A1 | 6/2009 | Katzen et al. |
| 2010/0189774 | A1 | 7/2010 | Lenormand |
| 2010/0190188 | A1 | 7/2010 | Henderson et al. |
| 2010/0233782 | A1 | 9/2010 | Katzen et al. |
| 2010/0291189 | A1 | 11/2010 | Yokoyama et al. |
| 2011/0104781 | A1 | 5/2011 | Katzen et al. |
| 2011/0195450 | A1 | 8/2011 | Kudlicki et al. |
| 2012/0270230 | A1 | 10/2012 | Henderson et al. |
| 2016/0052991 | A1 | 2/2016 | Henderson et al. |
| 2018/0086814 | A1 | 3/2018 | Henderson et al. |

FOREIGN PATENT DOCUMENTS

| | | |
|---|---|---|
| EP | 1176210 | 1/2002 |
| EP | 1316616 | 6/2003 |
| EP | 1354959 | 10/2003 |
| EP | 1384778 | 1/2004 |
| EP | 1507003 | 2/2005 |
| EP | 1857558 | 11/2007 |
| JP | 4-200390 | 7/1992 |
| JP | 7-110236 | 4/1995 |
| JP | 09-107954 | 4/1997 |
| JP | 09-234074 | 9/1997 |
| JP | 2000-325076 | 11/2000 |
| JP | 2002-238595 | 8/2002 |
| JP | 2003-235598 | 8/2003 |
| JP | 2004-091790 | 3/2004 |
| JP | 2004-215651 | 8/2004 |
| JP | 2004-267205 | 9/2004 |
| JP | 2004-290181 A | 10/2004 |
| JP | 2005-006646 | 1/2005 |
| JP | 2005-225796 | 8/2005 |
| JP | 2006-219401 | 8/2006 |
| WO | WO 88/08453 | 11/1988 |
| WO | WO 92/07949 | 5/1992 |
| WO | WO 92/11390 | 7/1992 |
| WO | WO 92/13955 | 8/1992 |
| WO | WO 97/046696 | 12/1997 |
| WO | WO 99/02671 | 1/1999 |
| WO | WO 99/14370 | 3/1999 |
| WO | WO 99/20798 | 4/1999 |
| WO | WO 99/57992 | 11/1999 |
| WO | WO 00-56914 | 9/2000 |
| WO | WO 01-83805 | 11/2001 |
| WO | WO 02/18586 | 3/2002 |
| WO | WO 02/090537 | 11/2002 |
| WO | 2003/097829 | 11/2003 |
| WO | 2009/060857 | 5/2009 |

OTHER PUBLICATIONS

Hendrickson, W. "Atomic-level analysis of membrane-protein structure" Nature Structural & Molecular Biology, Jun. 2016, vol. 23, No. 6, 464-467.
Naranjo, A.N. et al. "Impact of purification conditions and history on A2A adenosine receptor activity: The role of CHAPS and lipids" Protein Expression and Purification, 2016, pp. 1-18.
Glover, K. et al. Structural Evaluation of Phospholipid Bicelles for Solution-State Studies of Membrane-Associated Biomolecules. Biophysical Journal, vol. 81, 2001, 2163-2171.
Killian, J. A. et al. Peptides in lipid bilayers: the power of simple model. Current Opinion in Structural Biology, 2006, 16:473-479.
Duque, D. et al. Molecular theory of hydrophobic mismatch between lipids and peptides, Journal of Chemical Physics, vol. 116, No. 23, Jun. 2002, 10478-10484.
Ramadurai, S. et al. Influence of Hydrophobic Mismatch and Amino Acid Composition on the Lateral Diffusion of Transmembrane Peptides, Biophysical Journal, vol. 99, Sep. 2010, 1447-1454.

Pratt, J. M. et al., Transcription and translation—a practical approach, (1984), pp. 179-209, Henes, B. D. and Higgins, S. J. ed. , IRL Press, Oxford.
Baranov, V. I. and Spirin, A, Gene Expression in Cell-Free System on Preparative Scale, Methods in Enzymol., 217, 123-142, 1993.
Vold, R. et al. "Isotropic solutions of phospholipid bicelles: A new membrane mimetic for high-resolution NMR studies of polypeptides" Journal of Biomolecular NMR, 9 (1997) 329-335.
Matsumori, N. "Detailed Description of the Conformation and Location of Membrane-Bound Erythromycin A Using Isotropic Bicelles" J. Med. Chem. 2006, 49, 3501-3508.
Warschawski, D. "Choosing membrane mimetics for NMR structural studies of transmembrane proteins" Biochimica et Biophysica Acta 1808 (2011) 1957-1974.
Kim, H. J. et al. "Recent Advances in the Application of Solution NMR Spectroscopy to Multi-Span Integral Membrane Proteins" Prog Nucl Magn Reson Spectrosc. 2009; 55(4): 335-360.
Pogei, S. F. "Solution NMR of membrane proteins in bilayer mimics—small is beautiful, but sometimes bigger is better" Biochim Biophys Acta. Dec. 2007; 1768(12): 3098-3106.
Whiles, J. et al. "Bicelles in structure-function studies of membrane-associated proteins" Bioorganic Chemistry 30 (2002) 431-442.
Opekarova, M. and Tanner, W. Specific lipid requirements of membrane proteins—a putative bottleneck in heterologous expression. Biochim. Biophys. Acta 1610, 11-22 (2003).
Hanson, M.A. et al. A specific cholesterol binding site is established by the 2.8 A structure of the human β2-adrenergic receptor. Structure 16, 897-905 (2008).
Sonoda, Y. et al. Benchmarking membrane protein detergent stability for improving throughput of high-resolution X-ray structures. Structure 19, 17-25 (2011).
Ichikawa, S., et al., Expression cloning of a cDNA for human ceramide glucosyltransferase that catalyzes the first glycosylation step of glycosphingolipid synthesis. Proc. Natl. Acad. Sci. U S A 93, 4638-4643 (1996).
Komori, H., et al., Regulation of UDP-glucose: ceramide glucosyltransferase-1 by ceramide. FEBS Lett. 475, 247-250 (2000).
Tomita, T. Molecular mechanism of intramembrane proteolysis by γ-secretase. J. Biochem. 156, 195-201 (2014).
Watanabe, N. et al. Pen-2 is incorporated into the γ-secretase complex through binding to transmembrane domain 4 of presenilin 1. J. Biol. Chem. 280, 41967-41975 (2005).
Takeo, K. et al. Allosteric regulation of γ-secretase activity by a phenylimidazole-type γ-secretase modulator. Proc. Natl. Acad. Sci. U S A (2014). vol. 111, No. 29, 10544-10549.
Sonoda, N. et al. Clostridium perfringens enterotoxin fragment removes specific claudins from tight junction strands: Evidence for direct involvement of claudins in tight junction barrier. J. Cell Biol. 147, 195-204 (1999).
Hirata, K. et al. New micro-beam beamline at SPring-8, targeting at protein micro-crystallography. AIP Conf. Proc. 1234, 901-904(2010).
Hirata, K. et al. Achievement of protein micro-crystallography at SPring-8 beamline BL32XU. J. Phys. Conf. Ser. 425, 012002(2013), 1-5.
Otwinowski, Z. and Minor, W. Processing of X-ray Diffraction Data Collected in Oscillation Mode. Methods Enzymol., 307-326 (1997).
Kabsch, W. XDS. Acta Crystallogr. D Biol. Crystallogr. 66, 125-132 (2010).
Emsley, P., et al., K. Features and development of Coot. Acta Crystallogr. D Biol. Crystallogr. 66, 486-501 (2010).
Kalmbach, R. et al. "Functional Cell-free Synthesis of a Seven Helix Membrane Protein: In situ Insertion of Bacteriorhodopsin into Liposomes" J. Mol. Biol. (2007) 371, 639-648.
Lyukmanova, E.N. et al. Lipid-protein nanodiscs for cell-free production of integral membrane proteins in a soluble and folded state: Comparison with detergent micelles, bicelles and liposomes, Biochimica et Biophysica Acta 1818 (2012) 349-358.
Uhlemann, E.M. et al. "Cell-free synthesis of membrane subunits of ATP synthase in phospholipid bicelles: NMR shows subunit a fold similar to the protein in the cell membrane" Protein Science 2012 vol. 21:279-288.

(56) References Cited

OTHER PUBLICATIONS

Cho, H. S. et al. Lipid Domains in Bicelles Containing Unsaturated Lipids and Cholesterol, J. Phys. Chem. B 2010, 114, 9238-9245.
Laganowsky, A. "Membrane proteins bind lipids selectively to modulate their structure and function" Nature, 2014, vol. 510, 19 pages.
Hauser, H. Short-chain phospholipids as detergents, Biochimica et Biophysica Acta 1508 (2000) 164-181.
Zhao, X. et al. Designer short peptide surfactants stabilize G protein-coupled receptor bovine rhodopsin, PNAS, Nov. 2006, vol. 103, No. 47, 17707-17712.
Nagai, A. et al. Dynamic Behaviors of Lipid-Like Self-Assembling Peptide A6D and A6K Nanotubes, Journal of Nanoscience and Nanotechnology, vol. 7, 2007, pp. 1-7.
Agah, S. et al. Crystallization of Membrane Proteins in Bicelles, Methods in Molecular Biology, vol. 914, 2012, 16 pages.
Ram, P. et al. Magnetic field induced ordering of bile salt/phospholipid micelles: new media for NMR structural investigations, Biochimica et Biophysica Acta, 940 (1988) 289-294.
Sanders, C. Reconstitution of Membrane Proteins into Lipid-Rich Bilayered Mixed Micelles for NMR Studies, Biochemistry 1995, 34, 4030-4040.
Faham, S. et al. Bicelle Crystallization: A New Method for Crystallizing Membrane Proteins Yields a Monomeric Bacteriorhodopsin Structure, J. Mol. Biol (2002) 316, 1-6.
Shimono, K., et al., Production of functional bacteriorhodopsin by an *Escherichia coli* cell-free protein synthesis system supplemented with steroid detergent and lipid, 2009, Protein Science, vol. 18, p. 2160-2171 abstract.
International Search Report of PCT/JP2016/072444, dated Sep. 27, 2016, 2 pages.
International preliminary report on patentability of PCT/JP2016/072444, dated Feb. 6, 2018, 7 pages.
Office Action for U.S. Appl. No. 10/476,413, dated Jun. 20, 2005.
Office Action for U.S. Appl. No. 10/476,413, dated Dec. 23, 2004.
Office Action for U.S. Appl. No. 10/476,413, dated Aug. 11, 2004.
Office Action for EP Patent Application No. 088468269, dated Jan. 19, 2012, 7 pages.
Office Action for U.S. Appl. No. 12/741,575, dated Nov. 1, 2011.
Restriction Requirement for U.S. Appl. No. 12/741,575, dated Sep. 6, 2011.
Walter et al., Prepatation of Microsomal Membranes for Cotranslation Protein Translocation, Methods in Enzymology, vol. 96, pp. 84-93. 1983.
Merola et al., "Folding of hepatitis C virus E1 glycoprotein in a cell-free system", Journal of Virology, vol. 75, No. 22, pp. 11205-11217, 2001.
Kodukula at al., Biosynthesis of phosphatidylinositol-glycan (PI-G)-anchored membrane proteins in cell-free systems: PI-G is an obligatory cosubstrate for COOH-terminai processing of nascent proteins, Proc. Natl. Acad. Sci., vol. 89, No. 11, pp. 4982-4985, 1992.
Svitkin et al., "Complete transition of the hepatitis C virus genome in vitro: membranes play a critical role in the maturation of all virus proteins except for NS3". Journal of Viology, vol. 79, No. 11, pp. 6868-6881, 2005.
Evdokimova et al., "The major mRNA-associated protein YB-1 is a potent 5' capdependent mRNA stabilizer",The EMBO Journal, vol. 20, No. 19, pp. 5491-5502, 2001.
Emmerich et at, "Characterisation of Protein Synthesis in Cell-Free Extracts from Different Mammalian Cells by their Sensitivity to inhibitors of Polypeptide-Chain Initiation"., Hoppe-Seyler's Z. Physiol. Chem., vol. 360, No. 8, pp. 1099-1111, 1979.
Bulleid et al., "Cell-free synthesis of enzymically active tissue-type plasminogen activator", Biochem. J., vol. 286 (Part 1), pp. 275-280, 1992.
Office Action dated Aug. 10, 2010 in Japanese Application No. 2004-333250.

Cosgrove et al., "Absence of age diiferences in protein synthesis by rat brain, measured with an Initiating cell-free system", Neurobiology of Aging, vol. 8, No. 1, pp. 27-34. 1987.
Mori et at, "Cell-free translation of carbamyl phosphate synthetase I and ornithine transcarbamylase messenger RNAs of rat liver, Effect of dietary protein and fasting of translatable mRNA levels", Journal of Biological Chemistry, vol. 256, No. 8, pp. 4127-4132, 1981.
Hardwick et al. "Cell-free protein synthesis by kidney from the aging female fischer F344 rat", Biochimica et Biophysica Acta. vol. 652. No. 1, pp. 204-217. 1981.
Dougherty et al, "Translation of Potyvirus RNA in a Rabbit Reticuiocyte Lysate: Reaction Conditions and Identification of Capsid Protein as One of the Products of in Vitro Translation of Tobacco Etch and Pepper Mottle Viral RNAs", Virology, vol. 101, No. 2, pp. 466-474. 1980.
Cooper et al., "Transcription of Vaccinia Virus mRNA Coupled to Translation in Vitro", Virology. vol. 88, No. 1, pp. 149-165. 1978.
Weber et al., "inhibition of Protein Synthesis by Cl—". Journal of Biological Chemistry. vol. 252. No. 11, pp. 4007-4010. 1977.
Ikura et al.. "A novel approach for sequential assignement of 1H, 13C, and 15N spectra of proteins: heteronuclear triple resonance three-dimensional NMR spectroscopy. Application to calmodulin.". Biochemistry, vol. 29. pp. 4659-4667. 1990.
Paizlaff et al., "An isotope-edited FT-iR study of a symporter, the lactose permease", Biochem. vol 41. pp. 7366-7372, 2002.
Ikura M.,"Heteronuclear 3D NMR and isotopic labeling of calmodulin. Towards the complete assignment of the H NMR spectrum", Biochem, Pharmacol., vol. 40, No. 1. pp. 153-160, 1990.
Kigawa et at. "Cell-free synthesis and amino acid-selective stable isotope labeling of proteins for NMR analysis", Journal of Biomolecular NMR. vol. 6. No. 2. pp. 129-134. 1995.
Ge et at. "Simultaneous Introduction of Multiple Mutations Using Overlap Extension PCR", Biotechniques. vol. 22. No. 1. pp. 28 and 30. 1997.
Kigawa et al. "Structure Determination of Protein Folds Using the Cell-free Synthesis and NMR Spectroscopy", Experimental Medicine, vol. 18. No. 18. pp. 60-64. 2000.
Spirin et al., "A Continuous Cell-Free Translation System Capable of Producing Polypeptides in High Yield". Science. vol. 242. No. 4882. pp. 1162-1164. 1988.
Hendrickson. W., "Determination of Macromolecular Structures from Anomalous Diffraction of Synchrotron Radiation", Science, vol. 254, No. 5028, pp. 51-58, 1991.
Ha at at. "Immunostimulation with *Escherichia coli* extract: prevention of recurrent urinary tract infections", International Journal of Antimicrobial Agents. vol. 31S. pp. S63-S67, 2008.
Kigawa et al. "Preparation of *Escherichia coli* cell extract for highly productive cell-free protein expression". Journal of Structural and Functional Genomics. vol. 5. pp. 63-68, 2004.
Kim at al. "A highly efficient cell-free protein synthesis system from *Escherichia coli*". Eur. J. Biochem. vol. 239. pp. 881-886. 1996.
Sitaraman et a 1 . "A novel cell-free protein synthesis system". Journal of Biotechnology. vol. 110, pp. 257-263. 2004.
Lee et al. "Enhanced specific antibody productivity of calcium aiginate-entrapped hybridoma is cell line-specific", Cytotechnoiogy. vol. 16. pp. 1-15, 1994.
Pelham et al.. "An Efficient mRNA-Dependent Translation System from Reticulocyte Lysates", Eur. J. Biochem. vol. 67. pp. 247-256, 1976.
Mikami et al. "An efficient mammalian cell-free translation system supplemented with translation factors", Protein Expression and Purification. vol. 46. pp. 348-357, 2006.
Imataka et al., "A new translational regulator with homology to eukaryotic translation initiation factor 4G", EMBO Journal. vol. 16, No. 4, pp. 817-825, 1997.
Svitkin et at. "Poly(A)-bindlng protein interaction with eIF4G stimulates picornavirus IRES-dependent translation", RNA. vol. 7, pp. 1743-1752, 2001.
Imataka et al. "A newly identified N-terminal amino acid sequence of human eIF4G binds poly(A)-bindlng protein and functions in poly(A)-dependent translation". EMBO Journal. vol. 17, No. 24. pp. 7480-7489, 1998.

(56) References Cited

OTHER PUBLICATIONS

Nevins et al., "Distinct Regulation of internal Ribosome Entry Site-mediated Translation following Cellular Stress is Medicated by Apoptotic Fragments of elF4G Translation initiation Factor Family Members elF4GI and p97/DAP5/NAT1", Journal of Biological Chemistry. vol. 278. No. 6, pp. 3572-3579, 2003.
Scheper et at, "The 5' untranslated region of encephalomyocarditis virus contains a sequence for very efficient binding of eukaryotic initiation factor elF-2/2B", Biochimlca et Biophysica Acta. vol. 1089. pp. 220-226, 1991.
Scheper et al., "Eukaryotic initiation Factors-4E and -4F Stimulate 5' cap-dependent as Well as Internal initiation of Protein Synthesis", Journal of Biological Chemistry. vol. 267, No. 11, pp. 7269-7274, 1992.
Bergamini at al., "Picornavirus IRESes and the poly(A) tail jointly promote cap-independent translation in a mammalian cell-free system", RNA. vol. 6. pp. 1781-1790, 2000.
Morley et al., "A rabbit reticulocyte factor which stimulates protein synthesis in several mammaLian cell-free systems", Biochimica et Biophysica Acta, vol. 825, pp. 57-69. 1985.
Thoma et al. "A Poly(A) Tail-Responsive in Vitro System for Cap- or IRES-Driven Translation from HeLa Cells", Methods in Molecular Biol., vol. 257, pp. 171-180, 2004, XP002496677.
Preiss et al.. "Starting the protein synthesis machine: eukaryotic translation initiation", BioEssays. vol. 25, No. 12, pp. 1201-1211, 2003.
Pestova at al., "The structure and function of initiation factors in eukaryotic protein synthesis". Cell. Mol. Life Sci. vol. 57. pp. 651-674. 2000.
Person et al.. "Translation in Micrococcal nuclease-treated cell-free extracts from ehrlich ascites tumor cells". Biochimica et Biophysica Acta., vol. 783. pp. 152-157. 1984.
Henis-Korenblit et al., "The caspase-cleaved DAP5 protein supports internal ribosome entry site-mediated translation of death proteins". PNAS. vol. 99. No. 8, pp. 5400-5405. 2002.
Carroll et al.. "Preparation of a Cell-Free Translation System with Minimal Loss of initiation Factor elF-2/elF-2B Activity"—Analytical Biochemistry. vol. 212. pp. 17-23. 1993.
Kigawa. T. "Large-Scale Preparation of Proteins by the Cell-Free Synthesis". Biophysics., vol. 40. No. 6. pp. 391-394. 2000.
Lee at al.. "Statistical Medium Formulation and Process Modeling by Mixture Design of Experiment for Peptide Overexpression in Recombinant *Escherichia coli*". Applied Biochemistry and Biotechnology. vol. 135. pp. 81-100. 2006.
Ertola et al.. "Design, Formulation, and Optimization of Media". Bioprocess Technol.. vol. 21. pp. 89-137, 1995.
Kim et al.. "Continuous Cell-Free Protein Synthesis Using Glycolytic intermediates as Energy Sources". J. Microbiol. Biotechnol.. vol. 18, No. 5, pp. 885-888. 2008.
Kim et al.. "Expression-independent consumption of substrates in cell-free expression system from *Escherichia coli*". Journal of Biotechnology. vol. 84. pp. 27-32. 2000.
Hofbauer et al.. "Preparation of a mRNA-Dependent Cell-Free Translation System from Whole Cells of *Saccharomyces cerevisiae*", Eur. J. Biochem. vol. 122. pp. 199-203. 1982.
Wang et al.. "An Optimized Yeast Cell-Free System: Sufficient for Translation of Human Papillomavirus 58 LI mRNA and Assembly of Virus-like Particles". Journal of Bioscience and Bioengineering, vol. 106. No. 1. pp. 8-15. 2008.
Jones et al.. "Function of a Relaxed-Like State following Temperature Downshifts in *Escherichia coli*". Journal of Bacteriology, vol. 174. No. 12. pp. 3903-3914. 1992.
Zawada et al., "Effects of Genotype and Growth Conditions on Cell-Free Protein Synthesis Systems". Abstracts of Papers of the American Chemical Society. vol. 224. Nos. 1-2. p. BIOT91, 2002. XP009068071.
Mathews et al. "Mammalian Cell-Free Protein Synthesis Directed by Viral Ribonucleic Acid". Eur. J. Biochem. vol. 17. pp. 328-338. 1970.

Klammt et al, "Cell-Free Production of integral Membrane Proteins on a Preparative Scale". Methods in Molecular Biology. vol. 375. pp. 57-78. 2007.
Patterson et al., Deductive Analysis of a Protein-Synthesis Mutant of *Escherichia coli*., Biochemical Genetics. vol. 8. No. 2. pp. 205-230. 1973.
Shehata et al.. "Effect of Temperature on the Size of *Escherichia coli* Cells". Journal of Bacteriology. vol. 124. No. 2. pp. 857-862. 1975.
Timms et at. "Mutant sequences in the rpsL gene of *Escherichia coil* B/r: mechanistic implications for spontaneous and ultraviolet light mutagenesis". Molecular and General Genetics, vol. 232. pp. 89-96. 1992.
Funatsu et al., "Ribosomai Proteins: Location of Amino-acid Replacements in Protein S12 isolated from *Escherichia coli* Mutants Resistant to Streptomycin". J. Mol. Biol. vol. 68. pp. 547-550. 1972.
Inaoka et al., "Construction of an In Vivo Nonsense Readthrough Assay System and Functional Analysis of Ribosomal Proteins S12, S4. and S5 in Bacillus subtilis". Journal of Bacteriology, vol. 183. No. 17. pp. 4958-4963. 2001.
Office Action dated Jan. 13. 2009 in Japanese Application No. 2002-345597.
Hwang. Y.-i.. "Mutant 305 ribosomal subunit S12". Database EMBL. Oct. 1, 2002. XP-002353555.
Chumpolkulwong et al.. "Effects of *Escherichia coli* ribosomal protein S12 mutations on cell-tree protein synthesis". Eur. J. Biochem. vol. 271, pp. 1127-1134, 2004.
Hosoya et at. "Acquisition of Certain Streptomycin-Resistant (str) Mutations Enhances Antibiotic Production in Bacteria". Antimicrobial Agents and Chemotherapy, vol. 42. pp. 2041-2047. 1998.
Hu et al., "Novel Approach for Improving the Productivity of Antibiotic-Producing Strains by Inducing Combined Resistant Mutations". Applied and Environmental Microbiology, pp. 1885-1892, 2001.
Okamoto-Hosoya et al. "An aberrant protein synthesis activity is linked with antibiotic overproduction in rpsL mutants of Streptomyces coelicolor A3(2)". Microbiology. vol. 149. pp. 3299-3309. 2003.
Potapov et al. "Correlation between poly(U) misreading and poly(dT) translation efficiency in *E coli* cell-free systems". Biochimie. vol. 72. pp. 345-349. 1990.
Peng et at. "Cystic fibrosis transmembrane conductance regulator: expression and hellcity of a double membrane-spanning segment". FEBS Letters. vol. 431. No. 1, pp. 29-33. 1998.
Mambetisaeva et al.. "Expression of Three Functional Domains of Connexin 32 as Thioredoxin Fusion Proteins in *Escherichia coli* and Generation of Antibodies". Protein Expression and Purification. vol. 11. No. 1. pp. 26-34. 1997.
Ohtaki et at. "Expression, Purification, and Reconstitution of Receptor for Pituitary Adenylate Cyclase-activating Polypeptide". Journal of Biological Chemistry. vol. 273, No. 25. 15464-15473, 1998.
Rhee et at. "Channel-Forming Activity of Immunoaffinity-Purified Connexin32 in Single Phospholipid Membranes". Biochemistry. vol. 35. No. 28. pp. 9212-9223. 1996.
Falk. "Cell-free synthesis and assembly of connexins into functional gap junction membrane channels". EMBO Journal, vol. 16. No. 10. pp. 2703-2716. 1997.
Novagen. "pET-23a-d(+) Vectors". p. 1. 1998.
Invitrogen. "Flexible in vitro expression with high-yield results". Expressions. vol. 9. issue2, p. 7, 2002.
McIntyre et al.. "Procathepsins L and D are Membrane-Bound in Acidic Microsomal Vesicles. Journal of Biological Chemistry". vol. 266, No. 23 pp. 15438-15445, 1991.
Sachdev et at. "Solubility of Proteins Isolated from Inclusion Bodies is Enhanced by Fusion to Maltose-Binding Protein or Thloredoxin". Protein Expression and Purification. vol. 12. No. 1.,pp. 122-132, 1998.
Abdulaev et at. "Functionally Discrete Mimics of Light-activated Rhodopsin Identified through Expression of Soluble Cytoplasmic Domains". Journal of Biological Chemistry. vol. 275. No. 50. pp. 39354-39363. 2000.
Grisshammer et al., "Expression of a rat neurotensin receptor in *Escherichia coli*". Bicchem. Journal. vol. 295, pp. 571-576. 1993.

(56) References Cited

OTHER PUBLICATIONS

Tucker et al. "Purification of a rat neurotensin receptor expressed in *Escherichia coli*"., Biochem. Journal. vol. 317. pp. 891-899. 1996.
The pET Expression System, http://www.biodavidson.edu/Couree/Molblo?nolStudents/spring2003/Causey/p-ET.html. pp.1-4, 2003.
Lehto et at, "Release of the glycosyiphosphatidylinositol-anchored enzyme ecto-5'-nucleotidase by phospholipase C: catalytic activation and modulation by the lipid bilayer"., Biochem. Journal. vol. 332. pp. 101-109. 1998.
Yoshida et al.. "In Vitro Synthesis of Hyaluronan by a Single Protein Derived from Mouse HAS1 Gene and Characterization of Amino Acid Residues Essential for the Activity. Journal of Biological Chemistry". vol. 275. No. 1. pp. 497-506. 2000.
Laage et al.. "Strategies for Prokaryotic Expression of Eukaryotic Membrane Proteins",Traffic. vol. 2. No. 2, pp. 99-104. 2001.
Liu et ai.. "Functional characterization of novel human ARFGAP3", FEBS Letters. vol. 490.Nos. 1-2. pp. 79-83. 2001.
Horton et al.. "Engineering hybrid genes without the use of restriction enzymes: gene splicing by overlap extension". Gene. vol. 77. pp. 61-68. 1989. XP002090392.
Sandhu et al.. "Dual Asymmetric PCR: One-Step Construction of Synthetic Genes"., BioTechniques. vol. 12. No. 1. pp. 14-16. 1992. XP002134139.
Nakano et al.. "Efficient Coupled Transcription/Transiation from PCR Template by a Hollow-Fiber Membrane Bioreactor", Biotechnology and Bioengineering, vol. 64. No. 2. pp. 194-199. XP001084028.
Ohuchi et al.. "In vitro method for the generation of protein libraries using PCR amplification of a single DNA molecule and coupled transcription/transiation". Nucleic Acids Research. vol. 26. No. 19, pp. 4339-4346. 1998. XP002119037.
Macferrin et al.. "Overproduction and dissection of proteins by the expression-cassette polymerase chain reaction". Proc. Natl. Acad. Sci.. vol. 87, No. 5. pp. 1937-1941. 1990., XP000268593.
Kain et ai.. "Universal Promoter for Gene Expression Without Cloning: Expression-PCR".,BioTechniques, vol. 10. No. 3. pp. 366-368 and 370. 1991. XP000912135.
Kigawa et al. "High-throughput Cell-free Protein Expression System for Structural Proteomics". Protein. Nucleic Acid and Enzyme, vol. 47, No. 8, pp. 1014-1019. 2002.
Booth et al. Biochemical Society Transactions, vol. 28, Part 3. p. A50, 2000.
Kigawa et al., "Cell-free production and stable-isotope labeling of milligram quantities of proteins". FEBS Letters. vol. 442. pp. 15-19. 1999.
Wheatley et al., "Giycosylation of G-protein-coupled receptors for hormones central to normal reproductive functioning: its occurrence and role". Human Reproduction Update, 1999. vol. 5, No. 4, pp. 356-364.
Bochkareva et al., "Chaperonin-promoted Post-translational Membrane insertion of a Multispanning Membrane Protein Lactose Permease". Journal of Biological Chemistry. vol. 271. No. 36. pp. 22256-22261. 1996.

Sigma-Aldrich product catalog page for Polyoxyethylene 23 lauryl ether (Brij 35).
Nishimura et al.. "Enhancement of Protein Synthesis in Continuous-Flow. Cell-Free System by improvement of Membrane Permeation". Journal of Fermentation and Bioengineering. vol. 80. No. 4. pp. 403-405. 1995.
Giller et al.. "A homologous in vitro system to analyze transcription of a mouse Immunoglobulin u heavg-chain gene". Eur. J. Biochem. vol. 172. pp. 679-685. 1988.
Pain et al. "Analysis of Translational Activity of Extracts Derived from Oocytes and Eggs of Xenopus laevis", Methods in Molecular Biology. vol. 77. pp. 194-209. 1998. XP008075553.
Sawasaki T. et at. "In vitro protein synthesis system: Cell-free protein synthesis system prepared from wheat germ". Protein. Nocieic Acid and Enzyme. vol. 49. No. 11. pp. 1514-1519. 2004.
Abstract of Mikami S. et al. Protein Expression and Purification. Oct. 25, 2005.
Wieder K. J. et ai.. Proceedings of the National Academy of Sciences of USA. 1982. vol. 79., pp. 3599-3603.
Office Action dated Sep. 14. 2010 in Japanese Application No. 2004-335514.
Yang et al, "Cell-free coupled transcription-translation system for investigation of linear DNA segments". Proc. Natl. Acad. Sci.. vol. 77. No. 12. pp. 7029-7033. 1980.
Lorenz et al.. "Bacterial Gene Transfer by Natural Genetic Transformation in the Environment". Microbiological Reviews. vol. 58. No. 3, pp. 563-602, 1994.
Benzinger et al.. "Transfection of *Escherichia coil* Spheroplasts". Journal of Virology. vol. 15. No. 4. pp. 861-871. 1975.
Pratt et a l .. "Identification of gene products programmed by restriction endonuclease DNA fragments using an *E. coil* in vitro system". Nucleic Acids Research. vol. 9. No. 18, pp. 4459-4474. 1981.
Zubay, G., "in vitro synthesis of protein in microbial systems". Annual Review of Genetics. vol. 7. pp. 267-287. 1973.
Rowen et al., NCBi Protein AAF 02829. Submitted Apr. 25, 1999. Multimegabase Sequencelng Center. University of Washington.
Yu et al, An efficient recombination system for chromosome engineering in *Escherichia coli*.PNAS, vol. 97. No. 11. pp. 5978-5983, 2000.
Nishimura et al, "Cell-Free System Derived from Heat-Shocked *Escherichia coli*: Synthesis of Enzyme Protein Possessing Higher Specific Activity", Journal of Fermentation and Bioengineering, vol. 79. No. 2. pp. 131-135, 1995.
Giuliodori et al. "Preferential translation of cold-shock mRNAs during cold adaptation"., RNA, vol. 10. pp. 265-276. 2004.
Kalmbach R., et al. "Functional Cell-free synthesis of a Seven Helix Membrane Protein. In situ Insertion of Bacteriorhodopsin into Liposomes" J Mol. Biol, vol. 371 pp. 639-648(2007).
Ishihara, G., et al., "Expression of G protein coupled receptors in a cell-free translational system using detergents and thioredoxin-fusion vectors," Protein Expression and Pruflcation, vol. 41, pp. 27-37 (2005).

\* cited by examiner

T : TOTAL FRACTION
FT: flowthrough
W : WASH FRACTION
E : ELUTION FRACTION

T : TOTAL FRACTION
FT: flowthrough
W : WASH FRACTION
E : ELUTION FRACTION

FIG. 22
(a) PREPARED BICELLE ADDITION METHOD
q VALUE: 0.5
| DHPC, % | 2 |
|---|---|
| DMPC, % | 1 |
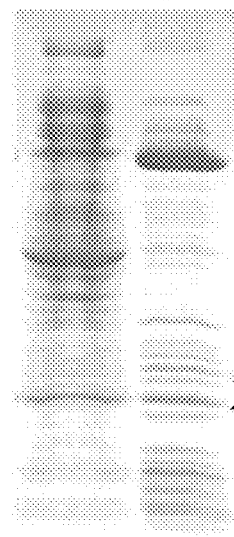
← CHANNEL A
(b) PRESENT INVENTION
DMPC/DHPC VALUE: 0.5
| DHPC, % | 2 |
|---|---|
| DMPC, % | 1 |
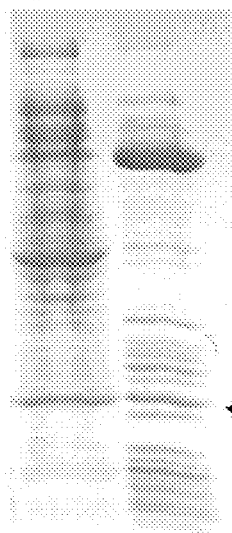
← CHANNEL A
(c) SYNTHESIS BY PRESENT INVENTION WITH LIPID-DETERGENT CONCENTRATION RATIOS COVERING WIDE RANGE OF CONCENTRATIONS
COMPARISON OF YIELDS WITH (b): 20%↓  28%↓  14%↓  62%↑  2%↑
DMPC/DHPC: 0.5   0.25   0.17   0.13   0.1
| DHPC, % | 1 | 2 | 3 | 4 | 5 |
|---|---|---|---|---|---|
| DMPC, % | 0.5 | 0.5 | 0.5 | 0.5 | 0.5 |
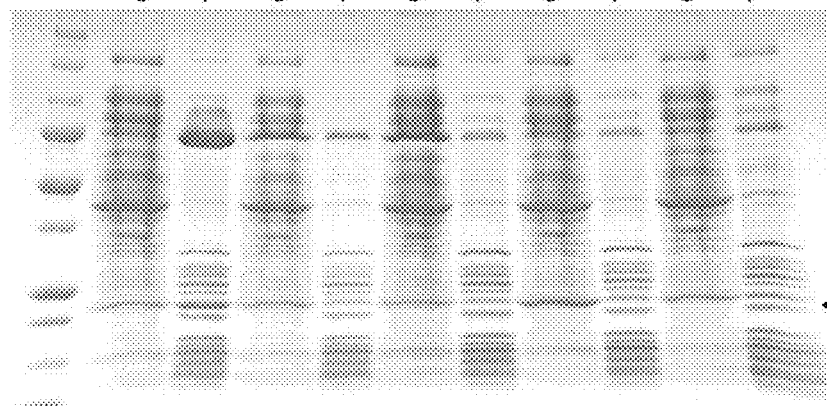
← CHANNEL A

METHOD OF MANUFACTURING MEMBRANE PROTEIN AND UTILIZATION THEREOF

Incorporated by reference in its entirety herein is a computer-readable nucleotide/amino acid sequence listing submitted concurrently herewith and identified as follows: One 1,000 Byte ASCII (Text) file named "37413-251_ST25" created on Dec. 8, 2021.

TECHNICAL FIELD

The present invention relates to, for example, (i) a novel method of producing a membrane protein and (ii) a composition containing the membrane protein which is produced by the novel method.

BACKGROUND ART

Primary structures of proteins encoded by genome in various organisms have been revealed based on results of various genome projects. Approximately 30% of proteins in higher organisms have been estimated to be an integral membrane protein having transmembrane helix. Membrane proteins are involved, for example, in signal transduction, mass transportation, energy production, and formation of cytoskeleton at cell membranes. In addition, membrane proteins are extremely important as a potential drug target. In fact, it is known that approximately 70% of commercially available pharmaceutical agents act on membrane proteins, particularly on a G protein-coupled receptor (GPCR). A large amount of samples having high purity are necessary for (i) use of membrane proteins for drug development and (ii) analysis of structure and function of membrane proteins. However, membrane proteins embedded in cell membranes unfortunately have low stability so as to be easily denatured during synthesis.

Membrane proteins can be synthesized mainly by a method in which a living cell expression system is used or a method in which a cell-free synthesis system is used. In a case where membrane proteins are produced with use of a living cell expression system, cell death may unfortunately occur due to low expression or overexpression, or it may unfortunately be difficult to extract the membrane proteins from a biomembrane. For example, in a case where membrane proteins are expressed in *E. coli*, the membrane proteins are ordinarily obtained as an inclusion body in which insoluble membrane proteins are incorrectly folded so as to be aggregated. This unfortunately leads to a small yield of membrane proteins which are naturally folded.

Meanwhile, in a case where membrane proteins are expressed in eukaryotic cells, solubilizing the membrane proteins with use of a detergent tends to cause the membrane proteins to be collected while being concentrated together with constituent molecules of a lipid raft in detergent-resistant membrane fractions (DRM) which is difficult to be dissolved with use of a detergent. DRM is a lipid raft which is present in cell membranes of animal cells, and refers to a lipid microdomain containing sphingolipid and cholesterol as main components. In DRM, important membrane proteins are accumulated, examples of which important membrane proteins encompass GPCR, G protein, ion channel, and claudin family protein. It is thus necessary to solubilize membrane proteins which are accumulated in a region where it is difficult to dissolve the membrane proteins. However, with a weak detergent whose effect on the properties of a membrane protein is small (i.e. less likely to, for example, cause denaturation to occur or cause a tertiary structure to be unstable), the efficiency in solubilizing the membrane protein is extremely low in many cases. Furthermore, it is in many cases necessary to use a strong detergent which may induce denaturation of membrane proteins. This tends to make it difficult to prepare membrane proteins which have biological activity and correct tertiary structures.

In order to address the instability of a membrane protein expressed in a living cell, there has been reported a technique in which the stability of a tertiary structure of a membrane protein is increased by introducing one or more mutations into a specific residue (Japanese Translation of PCT International Application, Tokuhyo, No. 2011-224018). However, it is reported that such a mutation changes the original tertiary structure of the membrane protein so as to largely affect the function of the membrane protein. It is therefore considered to be desirable that an artificial mutation is used in as small an amount as possible for (i) use of membrane proteins for drug development and (ii) analysis of structure and function of membrane proteins (Non-Patent Literature: Stabilization of functional recombinant cannabinoid receptor $CB_2$ in detergent micelles and lipid bilayers. October 2012).

Therefore, there have been attempts to use, in synthesis of membrane proteins, a cell-free synthesis system which makes it easy to artificially control the synthesis conditions. Examples of a method of synthesizing a membrane protein with use of a cell-free synthesis system encompass a method of producing, in the presence of a detergent, a membrane protein without insolubilizing the membrane protein (Japanese Patent Application Publication, Tokukai, No. 2003-18999). Although this method allows a many kinds of membrane proteins to be synthesized as soluble fractions in large amounts, it is necessary to reconstruct (refold) synthesized membrane proteins. This causes resulting membrane proteins to be different in quality from those which have been properly folded in a biological environment. For example, the resulting membrane proteins may be incorrectly folded (misfolded) (Non-Patent Literature: Stabilization of functional recombinant cannabinoid receptor $CB_2$ in detergent micelles and lipid bilayers. October 2012).

There have also been reported membrane protein synthesis methods in each of which liposome or lipid vesicle is prepared in advance and is then added to a cell-free synthesis system (Patent Literature 3, Patent Literature 4, and Non-Patent Literature 1). According to these methods, a lipid membrane, which has a continuous closed lipid bilayer structure, is formed in advance. Such a lipid membrane lacks a periphery into which a synthesized polypeptide chain can be easily inserted. In addition, the lipid membrane is closed entirely (stably formed). This causes insertion of a synthesized polypeptide chain into the lipid membrane to be markedly inefficient. Furthermore, the ease with which the polypeptide chain is inserted into the lipid bilayer structure is largely dependent on the properties of individual membrane proteins. This poses a serious problem with regard to yield and versatility (Non-Patent Literature: (Hydrophobic Mismatch Drives the Interaction of E5 with the Transmembrane Segment of PDGF Receptor)).

There has also been reported a method of synthesizing a membrane protein by integrating, in a cell-free protein synthesis system, a membrane protein into a nanodisc which has a multiple helical protein belt structure formed from an apolipoprotein (Patent Literature 5). A nanodisc is also closed entirely because it has a structure in which apolipoproteins are wound around a lipid disc. This leads to lacking of a periphery into which a polypeptide chain can be easily inserted. Therefore, with this method also, it is not possible to obtain a sufficient yield. It should be noted that, ordinarily, a membrane protein expressed in a living cell or the like is solubilized with a detergent DDM (n-dodecyl β-d-maltoside) and is then reconstructed into a nanodisc (Non-Patent Literature: "Reconstitution of Membrane Proteins in Phospholipid Bilayer Nanodiscs", Non-Patent Literature: "Atomic-level analysis of membrane-protein structure"). However, it has been reported that this solubilizing step leads to a decrease in binding affinity of a ligand with the membrane protein reconstructed into the nanodisc (Non-Patent Literature: "Impact of purification conditions and history on $A_{2A}$ adenosine receptor activity: The role of CHAPS and lipids"). In addition, for the purpose of crystallization or the like, it is necessary to remove, with use of a detergent or the like, the nanodisc which surrounds the membrane protein. This causes the membrane protein to be unsuited for structural analysis, etc. and therefore raises a problem with regard to versatility.

There has also been reported a method in which (i) a bicelle, which has been prepared in advance by mixing lipid and a detergent together at a specific concentration ratio, is added to a cell-free protein synthesis system and then (ii) a membrane protein is integrated into the bicelle and is synthesized (such a method will also be referred to as "prepared bicelle addition method") (Non-Patent Literatures 2 and 3). A bicelle is a disc-like lipid associated body having a lipid bilayer structure constituted by a long-chain phospholipid and short-chain phospholipid (detergent). The size, shape, and the like of a bicelle are adjusted by (i) a molar ratio (q value) between long-chain lipid and a detergent or (ii) the q value and a total lipid concentration ($C_L$ value) of a long-chain lipid concentration and a detergent concentration. While a membrane protein is being synthesized, it is necessary to maintain the q value or to maintain the q value and the $C_L$ value, so as to prevent the shape of the bicelle, which is stably formed, from changing. For example, in a case where the q value is maintained at 0.5, the $C_L$ value needs to be not less than 130 mM (Non-Patent Literature: (Structural Evaluation of Phospholipid Bicelles for Solution-State Studies of Membrane-Associated Biomolecules)). This makes it necessary to strictly control the q value in a reaction solution or to strictly control the q value and the $C_L$ value in the reaction solution. For this reason, Non-Patent Literature 3 and Non-Patent Literature 2 use a batch method and a dialysis method, respectively. According to Non-Patent Literature 2, a detergent is added to an external solution in an amount equivalent to an amount of detergent added to an internal solution, so as to prevent a q value from changing. In addition, since the kinds of lipid to be used are limited, there is a problem with regard to versatility in synthesizing various membrane proteins (Non-Patent Literature 4). Furthermore, it has been reported that the yield of membrane proteins having biological activity is unfortunately small (Non-Patent Literature 2).

There has been reported a method in which a steroidal detergent and phospholipid are used to produce a membrane protein folded in a lipid disc or in a liposome (Patent Literature 6). According to the method disclosed in Patent Literature 6, it is necessary to carry out a step of solubilizing the membrane protein folded in the lipid disc or in the liposome. This may affect the yield of membrane protein. In addition, according to this method, it is necessary to decrease a steroidal detergent concentration during a synthesis reaction of the membrane protein. This poses a problem that a detergent is substantially limited to a detergent which can be easily removed from a reaction system, i.e., a detergent having a small micellar size and/or having a high critical micelle concentration.

It has been reported that a lipid composition constituting a biomembrane varies depending on tissues, and that the thickness of a lipid bilayer also varies depending on tissues (Non-Patent Literature: (Peptides in lipid bilayers: the power of simple model)). Therefore, there are cases where the length of a hydrophobic region of a membrane protein does not necessarily match the thickness of a lipid bilayer prepared under conditions which are artificially limited. Then, for example, the degree to which this hydrophobic mismatch occurs may affect, for example, (i) the orientation in which a transmembrane helix is inserted into a membrane, (ii) the conformation in a lipid bilayer membrane, (iii) the constitution of the lipid, (iv) the curvature of the membrane, and (v) a membrane protein function (Non-Patent Literature: (Molecular theory of hydrophobic mismatch between lipids and peptides), Non-Patent Literature: (Influence of Hydrophobic Mismatch and Amino Acid Composition on the Lateral Diffusion of Transmembrane Peptides)). Non-Patent Literature (Hydrophobic Mismatch Drives the Interaction of E5 with the Transmembrane Segment of PDGF Receptor) reports that in a case where a papillomavirus-derived E5 protein (membrane protein) expressed in *E. coli* was integrated into a lipid bilayer membrane prepared in advance such as DMPC, a hydrophobic mismatch caused the E5 protein to be aggregated. This indicates that there are limits to the degree of application of the conventional techniques for integrating a membrane protein into, for example, liposome, lipid vesicle, bicelle, and nanodiscs which are prepared in advance.

Meanwhile, it has been reported that folding of a membrane protein, membrane protein structural stabilization, and a membrane protein function are regulated by binding a plurality of kinds of lipids to each other (Non-Patent Literature 5).

CITATION LIST

Patent Literature

Patent Literature 1
Japanese Translation of PCT International Application, Tokuhyo, No. 2011-224018
Patent Literature 2
Japanese Patent Application Publication, Tokukai, No. 2003-18999
Patent Literature 3
Japanese Patent Application Publication, Tokukai, No. 2005-225796
Patent Literature 4
Japanese Translation of PCT International Application, Tokuhyo, No. 2010-524488
Patent Literature 5
Japanese Translation of PCT International Application, Tokuhyo, No. 2009-521209
Patent Literature 6
PCT International Publication No. WO2009/060857 (Publication date: May 14, 2009)

Non-Patent Literature

Non-patent Literature 1
Kalmbach, R. et al., J. Mol. Biol. 371, 639-648 (2007)
Non-patent Literature 2
Lyukmanova E. N. et. al., Biochimica et Biophysica Acta 1818, 349-358 (2012)

Non-patent Literature 3
Eva-Maria E. Uhlemann et. al., Protein Science, Vol. 21, 279-288 (2012)
Non-patent Literature 4
Cho, H. S. et. al., J. Phys. Chem. B. 114, 9238-9245 (2010)
Non-patent Literature 5
Laganowsky, A. et. al., Nature 510, 172-175 (2014)
Non-patent Literature 6
Hauser. H. Biochimica et Biophysica Acta 1508, 164-181 (2000)
Non-patent Literature 7
Zhao, X. et al., PNAS, vol 103, no. 47, 17707-17712 (2006)
Non-patent Literature 8
Nagai, A., et al., Journal of Nanoscience and Nanotechnology Vol. 7, 1-7 (2007)
Non-patent Literature 9
Agah, S. et al., Membrane Protein Structure and Dynamics Dynamics: Methods and Protocols, Methods in Molecular Biology, vol. 914 (2012)
Non-patent Literature 10
Ram, P. et al., Biochimica et Biopharma Acta 940, 289-294 (1988)
Non-patent Literature 11
Sanders, C. R. et al., Biochemistry 34, 4030-4040 (1995)
Non-patent Literature 12
Faham, S. et al., J. Mol. Biol. 316, 1-6 (2002)

SUMMARY OF INVENTION

Technical Problem

According to the conventional methods of producing a membrane protein in a cell-free protein synthesis system, (i) a lipid membrane (particularly lipid bilayer membrane) is formed so that components are artificially prepared and then (ii) a membrane protein is integrated into the lipid membrane. However, the lipid membrane is not necessarily a suitable lipid membrane for reproducing a membrane protein in a biological environment. Such a lipid membrane lacks a periphery into which a synthesized polypeptide chain can be easily inserted. In addition, the lipid membrane is closed entirely. This causes insertion of a synthesized polypeptide chain into the lipid membrane to be markedly inefficient. As a technique for addressing this problem, Patent Literature 6 is reported. The technique is directed to a method in which a steroidal detergent and phospholipid are used to cause protein synthesis and lipid bilayer membrane formation to simultaneously proceed so as to produce a membrane protein folded in a lipid disc or in a liposome. This improves the yield. However, as in the cases of the conventional techniques, it is necessary to carry out a solubilizing step. In addition, there are cases where a strong detergent needs to be used for dealing with the formation of DRM when the membrane protein is solubilized. This may unfortunately induce the denaturation of the membrane protein. This may lead to a decrease in yield of membrane proteins which have biological activity and correct tertiary structures.

There are therefore demands for a technique in which a highly pure membrane protein having biological activity and a correct tertiary structure is synthesized by a method with a high yield and with excellent versatility.

Solution to Problem

As a result of diligent study in order to attain the object, the inventors of the present invention discovered the following. That is, in a cell-free protein synthesis system in which a detergent and lipids coexist, after translation of the membrane protein is started, without artificially decreasing a detergent concentration from an initial concentration, (i) the detergent and/or the lipid start(s) binding to a hydrophobic region of a polypeptide chain constituting the membrane protein or (ii) the lipid-detergent mixed micelle starts binding to the hydrophobic region of the polypeptide chain. Then, as the translation process proceeds while the hydrophobic region of the polypeptide chain is protected, the lipid and the detergent repeat selective association, substitution, and/or relocation, along the hydrophobic region of the polypeptide chain which is extending, which repetition occurs due to hydrophobic interaction, short-range interaction, hydrogen bond interaction, electrostatic interaction, or the like. This causes a suitable lipid to selectively bind to a suitable site. This causes an assembly of lipid-detergent-polypeptide chains to be gradually formed while the folding of the polypeptide chain is being corrected into a correct form. Therefore, a lipid-detergent mixed proteomicelle, in which a lipid and a detergent are bound to a membrane protein having a correct functional structure similar to that in a biological environment, can be efficiently produced as a final product. In other words, the inventors of the present invention successfully omitted a step of solubilizing a membrane protein and a step of reconstructing the membrane protein, which steps have been carried out in the conventional techniques. This established the technique with which a membrane protein having excellent quality can be obtained with a high yield. The present invention was thus completed.

In order to attain the object, a method in accordance with an aspect of the present invention for producing a membrane protein with use of a cell-free protein synthesis system includes: a step (a) of adding a template nucleic acid, a lipid, and a detergent to a reaction solution for cell-free protein synthesis, which template nucleic acid encodes a membrane protein; and a step (b) of synthesizing the membrane protein while a concentration of the detergent in the reaction solution is maintained at a concentration equal to or higher than a critical micelle concentration, the detergent and the lipid being added to the reaction solution without preparation in advance, which preparation causes a lipid membrane made of the detergent and/or the lipid to be stably formed.

A production method in accordance with an aspect of the present invention can further include a step (c) of collecting, from a supernatant of a centrifugate or from a purified eluate, a lipid-detergent mixed proteomicelle in which the lipid and the detergent are bound to the membrane protein.

An embodiment of the present invention provides a lipid-detergent mixed proteomicelle which is produced by the production method above and in which a lipid and a detergent are bound to a membrane protein.

Advantageous Effects of Invention

An aspect of the present invention provides a membrane protein production method which does not require the step of solubilizing a membrane protein and which allows the membrane protein having an excellent quality and to be obtained with versatility and with a high yield.

BRIEF DESCRIPTION OF DRAWINGS

FIG. 22 is a view illustrating yet another example of the present invention.

DESCRIPTION OF EMBODIMENTS

[Method of Producing Membrane Protein]

Figure 1:
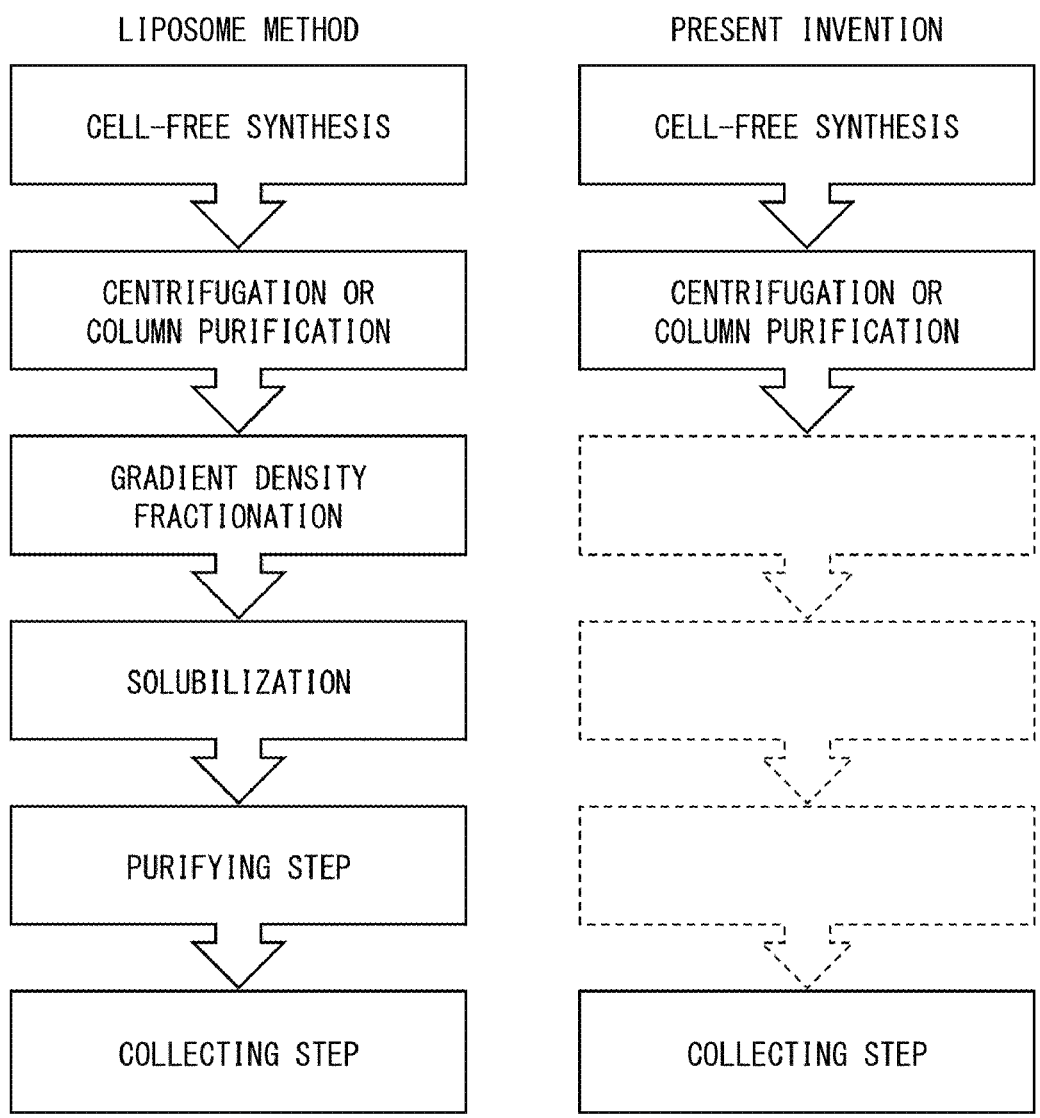
FIG. 1 is a view illustrating a difference in steps between the conventional technique (liposome method) and the method in accordance with an embodiment of the present invention.

A membrane protein production method in accordance with an embodiment of the present invention includes: a step (a) of adding a template nucleic acid, lipid, and a detergent to a reaction solution for cell-free protein synthesis, which template nucleic acid encodes the membrane protein; and a step (b) of synthesizing the membrane protein while a concentration of the detergent in the reaction solution is maintained at a concentration equal to or higher than a critical micelle concentration.

In the membrane protein production method in accordance with an embodiment of the present invention, the detergent and the lipid are added to the reaction solution for cell-free protein synthesis without preparation in advance which preparation cause a lipid membrane, which is made of the detergent and/or the lipid, to be stably formed.

According to an aspect of the present invention, in the step (b), after translation of the membrane protein is started, (i) the detergent and/or the lipid start(s) selectively binding to a hydrophobic region of a polypeptide chain or (ii) a lipid-detergent mixed micelle starts selectively binding to the hydrophobic region of the polypeptide chain. Then, as the translation process proceeds while the hydrophobic region of the polypeptide chain is protected, the lipid and the detergent can repeat selective association, substitution, and/or relocation, along the hydrophobic region of the polypeptide chain which is extending.

The membrane protein production method in accordance with an embodiment of the present invention can include a step of collecting, from the reaction solution for cell-free protein synthesis, a lipid-detergent mixed proteomicelle in which the lipid and the detergent are bound to the membrane protein.

An aspect of the membrane protein production method in accordance with an embodiment of the present invention can further include a step (c) of collecting, from a supernatant of a centrifugate or from a purified eluate, a lipid-detergent mixed proteomicelle in which the lipid and the detergent are bound to the membrane protein.

An aspect of the membrane protein production method in accordance with an embodiment of the present invention can further include, after the step (b), a step of carrying out centrifugation.

An aspect of the membrane protein production method in accordance with an embodiment of the present invention can further include, after the step (b), a step of carrying out purification by, for example, column chromatography or magnetic beads.

<Step (a)>

(Membrane Protein)

The term "membrane protein" herein refers to a protein which can interact with a lipid membrane (particularly lipid bilayer membrane). The term "membrane protein" includes, in addition to an integral membrane protein having a transmembrane helix or a barrel structure, (i) a protein having a portion as modified by palmitoylation, geranylation, myristoylation, or the like is embedded in membrane lipids or (ii) a protein which interacts with a membrane lipid or a membrane protein. Examples of the membrane protein encompass, but are not limited to, a receptor protein, a channel protein, a transporter (transporter protein), a membrane-bound enzyme, and a protein involved in cell adhesion. Many of these membrane proteins have important functions in a living body such as intracellular signal transduction and growth regulation, and are therefore extremely important as a target protein for drug development. In particular, an integral membrane protein having a transmembrane site(s) exhibits an extremely poorly water-soluble property because such an integral membrane protein has a hydrophobic amino acid sequence which arranged so as to be easily embedded into a membrane lipid. In a case where these membrane proteins are expressed in heterologous hosts by a recombinant DNA technology, the membrane proteins are quickly aggregated to form an insoluble precipitate. It is therefore difficult to prepare a protein which has biological activity and a correct tertiary structure.

A signal transduction pathway is a medically important biological pathway which is regulated by a second messenger such as a G protein and cAMP. Examples of a protein involved in this signal transduction pathway encompass, (i) a G protein-coupled receptor (GPCR) which binds to a ligand such as a peptide hormone and a neurotransmitter, (ii) a G protein itself, (iii) effector proteins such as phospholipase C, adenylate cyclase, and phosphodiesterase, (iv) protein kinase A, and (v) protein kinase C.

A GPCR super family, which is a membrane protein, is also called a 7-transmembrane receptor because the GPCR super family has seven transmembrane sites having an a helix structure. G protein to be coupled is ordinarily a trimer made up of alpha, beta and gamma subunits. It is known that an extremely large number of ligands bind to the GPCR. Examples of the ligand encompass dopamine, adrenaline, endothelin, adenosine, muscarine, acetylcholine, serotonin, histamine, thrombin, kinin, a taste component, and an olfactory component. Controlling the activity of this receptor is effective in treating nerve-related diseases, immunity-related diseases, blood pressure-related diseases, and metabolism-related diseases. A large number of receptors are identified by genomic analysis of eukaryotes, and a comprehensive research tool is needed. However, because GPCR is extremely hydrophobic due to its structure having seven transmembrane regions, conventional techniques pose such a problem that aggregation easily occurs in the case of large scale expression.

Other examples of cell membrane receptors encompass an ion channel receptor (such as glutamic acid receptor in brain). Examples of the transporter encompass a range of transporters such as (i) transporters for transporting a relatively low-molecular substance such as glucose or amino acid and (ii) transporters for transporting a relatively large molecule such as a protein or DNA.

Examples of the membrane-bound enzyme encompass many proteins involved in intracellular signal transduction, such as the G protein described above. The membrane-bound enzyme plays an important role concerning, for example, cell growth regulation and cell carcinogenesis.

Examples of the protein involved in cell adhesion encompass a claudin family protein. A claudin family 4-transmembrane protein is a main constituent element of a tight junction strand, and contributes to paracellular permeability and a barrier function. In a cell, claudin is localized in DRM described above. According to conventional methods that require a solubilizing step, therefore, there is no choice but to select a weak detergent in order to avoid denaturation of proteins. This causes solubilization to be incomplete. It is therefore difficult to produce a large amount of good-quality samples which cover a wide range of claudin protein families.

Furthermore, the membrane-bound enzyme includes not only such conventionally known membrane proteins, but also novel membrane proteins whose existence is expected from genomic information and whose functions are yet to be found.

Furthermore, a partial sequence, a homologous sequence, a modified sequence and a derivative of these proteins are included in the membrane protein in accordance with an embodiment of the present invention, provided that the protein basically interacts with a lipid membrane.

Furthermore, examples of the membrane protein in accordance with an embodiment of the present invention also encompass (i) a complex of membrane proteins and (ii) a complex constituted by proteins or the like which are not membrane proteins but include membrane proteins.

(Template Nucleic Acid)

To a reaction solution for cell-free protein synthesis, a template nucleic acid encoding a target membrane protein is added. A template nucleic acid encoding the membrane protein is, for example, a nucleic acid polymer of any length made up of ribonucleotides or deoxyribonucleotides. In addition, the template nucleic acid is a single-stranded DNA, a double-stranded DNA, a single-stranded RNA, or a double-stranded RNA. Furthermore, the template nucleic acid can be subjected to any conventionally known modification, and can be, for example, labeled with a fluorescent substance, methylated, added with a cap structure, or substituted with a nucleotide analog.

In the case of a DNA, the template nucleic acid is ordinarily double-stranded. In this case, the template nucleic acid can be a circular double-stranded DNA or a linear double-stranded DNA, which can be transcribed or translated in a cell-free protein synthesis system. These examples of the template nucleic acid can be produced by conventional recombinant DNA technologies which are known to a person skilled in the art, and in which E. coli and the like are used as a host. Alternatively, examples of the template nucleic acid can be prepared by techniques for in vitro DNA amplification, such as PCR, without transforming a host cell. In the case of RNA, the template nucleic acid is ordinarily used as a single-stranded mRNA, and translated in a cell-free protein synthesis system. These techniques are disclosed in, for example, (i) the literature: Sambrook et al., Molecular Cloning: A Laboratory Manual, Second Edition, 1989 and (ii) the literature: D. N Glover (ed.), DNA Cloning, Volumes I and II, 1985; M. J. Gait (ed.), Oligonucleotide Synthesis, 1984.

As a sequence necessary for transcription and/or translation in a cell-free protein synthesis system, for example, a sequence can be added, examples of which sequence encompass: (i) a potent promoter such as a T7 promoter, (ii) a ribosome binding site, and (iii) a T7 terminator. In addition, a tag sequence can be added, examples of which tag sequence encompass histidine, SUMO, StrepII, GST, and FLAG, each of which is intended for efficiently purifying an expressed fusion protein. Furthermore, a protease recognition site for cutting a tag sequence can be inserted between the tag sequence and a protein coding site.

(Critical Micelle Concentration)

The "critical micelle concentration (CMC)" is a concentration at which molecules of a detergent are assembled to start forming a micelle, and is a numerical value unique to detergents. The critical micelle concentration herein refers to CMC in pure water.

(Detergent)

The term "detergent" herein refers to a compound which exhibits a property of being adsorbed to a surface boundary of a solution so as to markedly change a state of the surface boundary. The term "detergent" also encompasses, for example, a short-chain phospholipid (Non-Patent Literature 6) which acts as a detergent. There is no particular limitation on the detergent for use in the present invention. According to the production method in accordance with an embodiment of the present invention, a wide range of kinds of detergents can be used. A detergent for use in an embodiment of the present invention can be mainly divided into ionic detergents and nonionic detergents.

Examples of the ionic detergent encompass 3-[(3-cholamidopropyl)dimethylammonio]-1-propanesulfonate (CHAPS), 3-[(3-cholamidopropyl)dimethylammonio]-2-hydroxypropanesulfonate (CHAPSO), 2,8-dimethyl-5-nonylphosphocholine (Fos choline iso-11), and diheptanoylphosphatidylcholine (DHPC).

Examples of the nonionic detergent encompass: polyoxyethylene-based detergents such as digitonin, polyoxyethylene alkyl ether (Brij-based), polyoxyethylene alkylphenyl ether (Triton-based), polyoxyethylene sorbitan (Tween-based), octylphenoxy polyethoxyethanol (Nonidet P-40), octaethylene glycol decyl ether ($C_{10}E_8$), octaethylene glycol dodecyl ether ($C_{12}E_8$), pentaethylene glycol dodecyl ether ($C_{10}E_5$), hexaethylene glycol dodecyl ether ($C_{12}E_6$), octyltetraoxyethylene, and octylpentaoxyethylene; glucoside/maltoside-based detergents such as octyl glucose neopentyl glycol (OG-NG), decyl maltose neopentyl glycol (DM-NG), n-decyl-β-D-maltopyranoside (DM), n-octyl-β-D-glucopyranoside (OG), n-nonyl-β-D-glucopyranoside (NG), n-undecyl-β-D-maltopyranoside (UDM), n-dodecyl-β-D-maltopyranoside (DDM), dodecyl maltose neopentyl glycol (DDM-NG), n-tridecyl-β-D-maltopyranoside (TDM), 4-cyclohexyl-1-butyl-β-D-glucopyranoside (Cy-Glu-4), 6-cyclohexyl-1-hexyl-β-D-maltopyranoside (Cy-Mal-6), 2,6-dimethyl-4-heptyl-β-D-maltopyranoside (DMHM), β-hepthyl-heptylthioglucoside (HTG), and β-octylthioglucoside (OTG); sucrose monodecanoate; and sucrose monododecanoate.

Preferable examples of the detergent encompass digitonin, polyoxyethylene alkyl ether (Brij-based), polyoxyethylene alkylphenyl ether, (Triton-based), octaethylene glycol decyl ether ($C_{10}E_8$), octaethylene glycol dodecyl ether ($C_{12}E_8$), octyl glucose neopentyl glycol (OG-NG), decyl maltose neopentyl glycol (DM-NG), n-undecyl-β-D-maltopyranoside (UDM), n-dodecyl-β-D-maltopyranoside (DDM), dodecyl maltose neopentyl glycol (DDM-NG), 6-cyclohexyl-1-hexyl-β-D-maltopyranoside (CyMal-6), and diheptanoylphosphatidylcholine (DHPC). More preferable examples of the detergent encompass digitonin, polyoxyethylene alkyl ether (Brij-based), polyoxyethylene alkylphenyl ether (Triton-based), octaethylene glycol decyl ether ($C_{10}E_8$), octyl glucose neopentyl glycol (OG-NG), decyl maltose neopentyl glycol (DM-NG), and diheptanoylphosphatidylcholine (DHPC).

One kind of these detergents can be used, or two or more kinds of these detergents can be used in combination. In the reaction solution for cell-free protein synthesis in the step (a), a detergent concentration can be set as appropriate according to, for example, the kind of a target membrane protein and the kind of the detergent, provided that the detergent concentration is at least a critical micelle concentration. A detergent, which may inhibit a synthesis reaction, can be used for an embodiment of the present invention, provided that the detergent concentration is low, for example, a critical micelle concentration. In the reaction solution for cell-free protein synthesis in the step (a), for example, the detergent concentration is preferably a concentration equal to or higher than the critical micelle concentration, and more preferably 1.0 times to 3000 times higher than the critical micelle concentration. For example, in a case where digitonin is used as a detergent, the detergent concentration is preferably 0.4% (w/v) to 3.0% (w/v), and more preferably 0.8% (w/v) to 1.2% (w/v). In a case where Brij-78 is used as a detergent, the detergent concentration is preferably 0.4% (w/v) to 3.0% (w/v), and more preferably 0.6% (w/v) to 1.0% (w/v).

The "state in which a detergent concentration is maintained at a concentration equal to or higher than a critical micelle concentration" means a state in which the detergent concentration is maintained in a range of concentrations which are equal to or higher than the critical micelle concentration and at which neither micelles nor lipid-detergent mixed micelles are fused with each other to grow, so that a lipid membrane is prevented from being stably formed. The "concentration range in which neither micelles nor lipid-detergent mixed micelles are fused with each other to grow, so that a lipid membrane is prevented from being stably formed" is a range of concentrations at which it is maintained that (i) the lipid-detergent mixed micelles are not prevented from growing so as to form a periphery into which a polypeptide chain can be easily inserted or (ii) the lipid and the detergent are not prevented from repeating selective association, substitution, or relocation. Such a concentration range varies depending on the kind of the detergent and on the kind of the lipid. Note, however, that such a concentration range can be found by a person skilled in the art, without an excessive amount of burden, through merely testing several concentration conditions as demonstrated in Example 1 (described later). Note that the term "micelle" refers to an assembly formed by amphipathic molecules associating with each other through hydrophobic interaction. The term "lipid-detergent mixed micelle" refers to a lipid-detergent assembly which is formed by a mixture of two or more kinds of substances containing amphipathic molecules which can form at least one micellar structure. Specifically, the "lipid-detergent mixed micelle" refers to a lipid-detergent assembly formed by a mixture of a detergent and lipid.

(Lipid)

The term "lipid" herein refers to any fatty acid derivative in which a hydrophilic portion and a hydrophobic portion are oriented externally (aqueous phase) and internally, respectively, so that a bilayer can be formed. In addition, examples of the lipid also encompass substances which can work as lipid (such a substance will be hereinafter also referred to as "lipid-like substance") such as peptide detergents (Non-Patent Literature 7 and Non-Patent Literature 8). Examples of the hydrophilic portion encompass a phosphate group, a carboxyl group, a sulfate group, an amino group, and a nitro group. Examples of the hydrophobic portion encompass (i) a long-chain (saturated/unsaturated) hydrocarbon group and (ii) a long-chain (saturated/unsaturated) hydrocarbon group which is substituted with at least one aromatic group, alicyclic group, or heterocyclic group. The term "lipid" encompasses not only natural lipid but also artificial lipid. Lipids for use in the present invention are not limited to any particular one. Examples of the lipid encompass phosphatidylcholine (PC), phosphatidylethanolamine (PE), phosphatidylserine (PS), phosphatidylinositol (PI), phosphatidylglycerol (PG), phosphatidic acid, sphingolipid, glycerophospholipid, cholesterol, lysophosphatidylcholine (lyso-PC), dipalmitoylphosphatidylcholine (DpPC), lysophosphatidylethanolamine (lyso-PE), lysophosphatidylserine (lyso-PS), galactosylceramide (GalCer), glucosylceramide (GlcCer), cardiolipin, egg-yolk lecithin, soybean lecithin, 1,2-dimyristoyl-sn-glycero-3-phosphocholine (DMPC), and lipids labeled with hydrogenated additives, fluorescent substances, and purification tags of these lipids. In addition, various mixtures of lipids, such as a porcine brain-derived lipid extract, can be used.

One kind of these lipids can be used, or two or more kinds of these lipids can be used in combination. It is therefore possible to select a plurality of kinds of lipids in combination, which lipids are suited for respective membrane proteins and are important for synthesizing membrane proteins having a biofunction. These lipids can be used in an amount set as appropriate according to the kind of a target protein. For example, the lipid(s) is preferably used in an amount 0.025 times to 2.0 times as much as the amount of the detergent used in the step (a) in terms of a weight ratio. In addition, as demonstrated in Examples described later, the present invention is markedly different from the conventional techniques in that a highly pure membrane protein, which has biological activity and a correct tertiary structure, can be obtained with a high yield by not only using a suitable lipid selected from a plurality of kinds of lipids but also, for example, (i) adding a lipid mixture containing a variety of lipids to a reaction solution so as to cause the membrane protein to select a lipid (or a plurality of kinds of lipids in some cases), (ii) using a lipid identified by analyzing an unknown lipid derived from a lipid mixture binding to the membrane protein as a result of the selection, or (iii) using a known lipid disclosed in literature and the like.

Unlike a bicelle (Non-Patent Literatures 9 through 12), a lipid-detergent mixed micelle in accordance with an embodiment of the present invention does not require considering any of the following in a case where a lipid and a detergent are to be combined: (i) the chain lengths of the lipid and the detergent, (ii) a q value, and (iii) a q value and a $C_L$ value. According to an embodiment of the present invention, it is also unnecessary to carry out a step of repeating a cycle of heating, cooling, and use of a vortex mixer (Non-Patent Literature 9) for uniformly mixing a lipid and a detergent. The lipid-detergent mixed micelle in accordance with an embodiment of the present invention is thus markedly different from a bicelle. Note, however, that it is possible with an embodiment of the present invention to use a combination of lipids and a detergent for use in preparation of a bicelle. Concrete examples of such a combination encompass a combination of (i) a long-chain lipid (such as DMPC, dipalmitoylphosphatidylcholine (DPPC), and 1-myristoyl-2-[4-(4-biphenyl)butanoyl]-sn glycero-3-phosphocholine (TBBPC)) and (ii) a short-chain lipid (such as DHPC, CHAPS, and CHAPSO) serving as a detergent.

Of course, in a case where lipids for use in preparation of a bicelle are used in combination with a detergent in an embodiment of the present invention, it is unnecessary to prepare a bicelle in advance or to set, in advance, (i) a q value or (ii) a q value and a $C_L$ value. In addition, the concentration of the combination can be selected by conducting a search for each concentration demonstrated in Example 1 described later.

(Cell-Free Protein Synthesis System)

A cell-free protein synthesis system used in the method in accordance with an embodiment of the present invention is a system in which a protein is in vitro synthesized with use of a cell extract solution and/or a reaction solution for cell-free protein synthesis, which reaction solution contains a reagent necessary for the synthesis. Examples of such system encompass (i) a cell-free translation system in which information of mRNA is read and a protein is synthesized on a ribosome and (ii) a system including both the cell-free translation system and a cell-free transcription system in which RNA is synthesized with use of DNA as a template. In a case where DNA is used as a template, simultaneous parallel preparation of numerous template DNAs can be carried out rapidly by an in vitro amplification reaction, such as PCR, without such a complicated manipulation as cloning which was required conventionally.

Examples of the cell extract solution encompass an extract solution which is obtained from a eukaryotic cell or a prokaryotic cell which contains components necessary for protein synthesis, such as a ribosome and tRNA. The eukaryotic cell and the prokaryotic cell can be any conventionally known cells. Concrete examples of such cells encompass *E. coli*, thermophilic bacteria, wheat germ, rabbit reticulocyte, mouse L cell, Ehrlich ascites carcinoma cell, HeLa cell, CHO cell, and budding yeast. In particular, cell extract solution derived from *E. coli* (e.g., *E. coli* S30 cell extract solution) or from extreme thermophile (*Thermus thermophilus*) is preferable due to their abilities to achieve high synthetic yield. The *E. coli* S30 cell extract solution can be prepared from, for example, *E. coli* A19 (rna, met), BL21, BL21 star, and BL21 codon plus strain according to known methods (see the literature: Pratt, J. M. et al., Transcription and translation—a practical approach, (1984), pp. 179-209, Henes, B. D. and Higgins, S. J. ed., IRL Press, Oxford), or can be an extract solution commercially available from Promega, Novagen, or the like.

A concrete method of preparing *E. coli* S30 extract solution is carried out such that *E. coli* cells are cultured and collected by subjecting the bacterial cells to centrifugation or the like. The collected bacterial cells are (i) washed, (ii) resuspended in a buffer solution, and then (iii) crushed with use of French press, glass beads, Waring blender, or the like. Insoluble substances of the crushed *E. coli* cells are removed by centrifugation, and the remaining is mixed with a preincubation mixture solution, and is then incubated. This causes endogenous DNA and RNA to be degraded. In addition, it is possible to degrade endogenous nucleic acids by adding, for example, (i) a calcium salt and (ii) a nuclease from *Micrococcus*. Subsequently, endogenous amino acid, nucleic acid, nucleoside, and the like are removed by dialysis. Then, the resulting solution is dispensed in proper amounts and preserved in liquid nitrogen or at −80° C.

The reaction solution in accordance with an embodiment of the present invention for cell-free protein synthesis can contain a substance(s) in addition to the cell extract solution such as *E. coli* S30. Examples of the substance(s) encompass templates such as DNA and mRNA, template nucleic acid encoding a membrane protein (such as mRNA), a detergent, lipid, ATP, GTP, CTP, UTP, a buffer solution, salts, amino acid, an inhibitor of nuclease, and an antibacterial agent. As necessary, RNA polymerase (in a case where DNA serves as a template) and/or tRNA can be contained. Other than the above, an ATP regenerating system, polyethylene glycol (e.g., PEG #8000), 3',5'-cAMP, folic acids, a redox regulating agent, enzyme, vesicle, protein chaperone, signal recognition particles, and/or other reagents can be contained. These synthesis reaction systems are known to a person skilled in the art, and are reported in literature.

Examples of the buffer encompass buffer agents such as Hepes-KOH and Tris-OAc. Examples of the salts encompass acetates (such as ammonium salt and magnesium salt) and glutamate. Examples of the antibacterial agent encompass sodium azide and ampicillin. In a case where DNA is used as a template, an RNA polymerase is added to the reaction system. In so doing, a commercially available enzyme such as a T7RNA polymerase can be used.

In an embodiment of the present invention, the ATP regenerating system includes a combination of creatine kinase (CK) in an amount of preferably 0.02 µg/µL to 5 µg/µL and creatine phosphate (CP) in an amount of preferably 10 mM to 100 mM. However, a material to be included in the ATP regenerating system is not limited to such a combination, but can be any conventionally known material. Other examples of the material encompass a combination of phosphoenol pyruvate (PEP) in an amount of 1 mM to 20 mM and pyruvate kinase (PK) in an amount of 0.01 µg/µL to 1 µg/µL. Each of these PK and CK are an enzyme which regenerate ATP from ADP, and require PEP and CP, respectively, as substrates.

<Step (b)>

In the step (b), a membrane protein is synthesized in the cell-free protein synthesis system described above. In so doing, a detergent concentration in the reaction solution for cell-free protein synthesis is maintained at a concentration equal to or higher than a critical micelle concentration. This causes lipid-detergent mixed micelles to be formed. It is considered, however, that because neither the micelles nor the lipid-detergent mixed micelles are fused with each other, neither the micelles nor the lipid-detergent mixed micelles grow so as to form a lipid membrane which is stably formed. A lipid membrane which is stably formed contains, for example, lipid vesicle, liposome, nanodisc, and bicelle. Note that the term "stably formed" refers to a structure which is formed by a continuous lipid bilayer membrane and is closed entirely. Such a lipid membrane lacks a periphery into which a synthesized polypeptide chain can be easily inserted. This makes it difficult for a translated polypeptide chain to be inserted into the lipid membrane, so that the formation of the lipid-detergent mixed proteomicelles becomes extremely inefficient. For example, a bicelle has a bilayer structure having a flat portion where a long-chain lipid is present. A periphery of a rim portion is stabilized by a detergent. A bicelle is stably formed by in such a manner as to depend on a combination of lipids and a detergent and by adjusting (i) a q value or (ii) a q value and a $C_L$ value. This puts restriction on the selection of suitable lipids or the like for each of membrane proteins having widely varying properties. Furthermore, since the periphery is stabilized, it may be difficult to insert a translated polypeptide chain. A nanodisc is closed entirely because it has a structure in which apolipoproteins are wound around a lipid disc. This makes it difficult to insert a translated polypeptide. In a case where lipid-detergent mixed micelles are fused with each other to grow so that a large lipid membrane (liposome) is stably formed, there is unfortunately an increased possibility that a lipid membrane is precipitated while impurities are introduced in the lipid membrane. In addition, it is also necessary to carry out the step of solubilizing precipitated proteoliposome before a purifying step. This may cause dissociation of lipids, binding of which is important for the formation of a membrane protein, to be broken, and therefore may pose the following possible problems: (i) the quality of the membrane protein deteriorates, (ii) the function and structure of the membrane protein are disrupted, or (iii) it becomes necessary to use a strong detergent for dealing with the formation of DRM, so that the denaturation of the membrane protein occurs. This may cause a decrease in yield of membrane proteins having biological activity and a correct tertiary structure. Note that a liposome is stably formed through the growth of a lipid membrane which occurs in a case where, for example, a detergent concentration is gradually decreased in the co-existence of lipids. According to an embodiment of the present invention, a detergent concentration is maintained at a concentration equal to or higher than the critical micelle concentration, and lipid-detergent mixed proteomicelles are formed while lipids suited for a membrane protein are selected (bound). This renders the present invention different from a method in which a lipid and a detergent are artificially grown into a liposome. Needless to say, the present invention is different from lipid vesicles, liposomes, bicelles, and the like which are prepared in advance.

According to an embodiment of the present invention, a detergent concentration in a reaction solution for cell-free protein synthesis is maintained in a range of concentrations at which neither micelles nor lipid-detergent mixed micelles are fused with each other, so that a lipid membrane is prevented from being stably formed. Therefore, after translation of the membrane protein is started, (i) the detergent and/or the lipid start(s) binding to a hydrophobic region of a polypeptide chain constituting the membrane protein or (ii) the lipid-detergent mixed micelle starts binding to the hydrophobic region of the polypeptide chain. Then, as the translation process proceeds while the hydrophobic region of the polypeptide chain is protected, the lipid and the detergent repeat selective association, substitution, and/or relocation, along the hydrophobic region of the polypeptide chain which is extending, which repetition occurs due to hydrophobic interaction, short-range interaction, hydrogen bond interaction, electrostatic interaction, or the like. This causes a suitable lipid to bind to a suitable site. This causes an assembly of lipid-detergent-polypeptide chains to be gradually formed while the folding of the polypeptide chain is being corrected into a correct form. A final product is therefore considered to be obtained efficiently in the form of a lipid-detergent mixed proteomicelle enclosed in a lipid-detergent assembly in a minimum amount necessary for the membrane protein to have a correct form. In the step (b), neither the detergent concentration before the synthesis reaction nor the detergent concentration after the completion of the synthesis reaction is limited to any particular concentration, provided that these detergent concentrations are each equal to or higher than a critical micelle concentration. The term "a lipid and a detergent repeat selective association, substitution, and/or relocation" refers to repetition of an operation in which the detergent or a lipid molecule is associated with (bound to) a hydrophobic region of a membrane protein, and then the lipid molecule is associated with the binding detergent, so that (i) the detergent is substituted with a lipid which binds to a site important for structural stability or functional regulation of the membrane protein and/or (ii) the binding lipid is substituted with a detergent binding to a more suitable site and is relocated. This presumably causes lipids to each selectively bind to a specific position of the membrane protein, which lipids are (i) lipids which are involved in the correct formation of conformation of membrane proteins and (ii) lipids which are involved in functional regulation.

The term "lipid-detergent mixed proteomicelle" refers to a lipid-detergent assembly in which a membrane protein is enclosed by lipids and a detergent. The term "enclose" refers to a state in which an assembly of lipids, a detergent, and a membrane protein is gradually formed through association, substitution, and/or relocation is/are selectively repeated along a hydrophobic region of a polypeptide chain of the membrane protein, which hydrophobic region is extending as the translation proceeds. Meanwhile, the term "integrate" refers to a state in which a membrane protein is inserted into (i) a lipid membrane which has been stably formed in advance or (ii) a lipid membrane which has been artificially stably formed. Therefore, the present invention is markedly different from the conventional techniques in which (i) a liposome formed through preparation in advance is integrated into a membrane protein (Non-Patent Literature 1), (ii) a bicelle is integrated into a membrane protein (Non-Patent Literature 2, Non-Patent Literature 3), (iii) a lipid vesicle is integrated into a membrane protein (Patent Literature 4), and (iv) a nanodisc is integrated into a membrane protein (Patent Literature 5, Patent Literature 8). Conventionally, techniques have been developed for increasing the stability of a lipid membrane environment such as bicelles. The present invention is completely different in that a detergent concentration is maintained at a concentration equal to or higher than a critical micelle concentration so that neither micelles nor lipid-detergent mixed micelles are fused with each other to grow so that a lipid membrane is not stably formed.

It was surprising to discover a phenomenon that during the process in which a membrane protein, lipid molecules, and detergent molecules spontaneously form an assembly so as to be self-organized, the detergent and lipids binding to sites that are important for structural stability and functional regulation of the membrane protein are replaced.

In the reaction solution for cell-free protein synthesis in the step (b), for example, the detergent concentration is preferably a concentration equal to or higher than the critical micelle concentration, and more preferably 1.0 times to 3000 times higher than the critical micelle concentration. The detergent concentration in each of the step (a) and the step (b) is not particularly limited, provided that the detergent concentration is a concentration equal to or higher than the critical micelle concentration.

To the cell-free protein synthesis system in accordance with an embodiment of the present invention, a batch method, a flow method, a dialysis method, and other known techniques (for example, see the literature: Spirin, A et al., Methods in Enzymol., 217, 123-142, 1993) can be applied. In a case where the dialysis method is employed, it is preferable that an internal solution and an external solution are separated via a dialysis membrane (ultrafilter) during shaking or stirring. As equipment for dialysis, for example, DispoDialyzer (registered trademark) (Spectrum), Slidealyzer (registered trademark) (Pierce) or Spectra/Por (registered trademark) dialysis tube (Spectrum) may be used. The detail of a cell-free protein synthesis system using a dialysis method which has been improved by the inventors of the present invention is disclosed in the literature: Japanese Patent Application Publication, Tokukai, No. 2000-175695, the disclosure of which is incorporated herein in its entirety by reference thereto. In a case where the dialysis method is carried out, the detergent concentration in the internal solution can be maintained at a concentration equal to or higher than a critical micelle concentration by, for example, (i) selecting a detergent which does not pass through a dialysis membrane, (ii) preventing a detergent from passing through a dialysis membrane through adjusting the pore size of the dialysis membrane, (iii) supplementing a detergent into the internal solution (through, for example, titration), or (iv) adding a detergent to an external solution.

<Step (c)>

According to the membrane protein production method in accordance with an embodiment of the present invention, it is possible to collect, from a reaction solution for cell-free protein synthesis, the membrane protein which has been produced in the step (b) and which is enclosed in a lipid-detergent assembly. For example, the membrane protein can be collected through centrifugation and/or purification (by use of, for example, column chromatography, magnetic beads, or the like).

In an aspect of the production method in accordance with an embodiment of the present invention, the membrane protein can be separated while in the form of lipid-detergent mixed proteomicelles through directly purifying the lipid-detergent mixed proteomicelles in which the lipid and the detergent bind to the membrane protein produced in the step (b). Note that a centrifugation step can be included before the purifying step.

A centrifugal force during the centrifugation is not particularly limited. However, the centrifugal force is preferably not less than 5,000 g from the perspective of separating as much unnecessary components as possible, which unnecessary components are, for example, an aggregate of the membrane protein which was not enclosed in the lipid-detergent assembly.

A temperature during the centrifugation is not particularly limited. However, the temperature is preferably 4° C. to 30° C. and more preferably 4° C. to 10° C. in view of the quality of the membrane protein. A period of the centrifugation is not particularly limited. However, the period is preferably 1 minute to 16 hours in view of a balance between removal of fine particles and operation efficiency.

According to the production method in accordance with an embodiment of the present invention, a membrane protein enclosed in a lipid-detergent assembly is obtained as a lipid-detergent mixed proteomicelle, and is then separated into a supernatant of a centrifugate. With the production method in accordance with an embodiment of the present invention, therefore, it is possible to collect the membrane protein from the supernatant of the centrifugate.

According to the technique disclosed in Patent Literature 6, a proteoliposome containing a membrane protein is separated into a precipitate as a result of centrifugation. In order to collect a membrane protein from a proteoliposome, it is necessary to carry out solubilization after the centrifugation. There are also cases where refinement is carried out by gradient density fractionation before the solubilization. In contrast, according to the production method in accordance with an embodiment of the present invention, it is unnecessary to carry out solubilization because a membrane protein is collected from a supernatant. In addition, since column purification and purification by magnetic beads or the like are easy, it is also unnecessary to carry out a refining step by gradient density fractionation. Therefore, because such steps are unnecessary according to an embodiment of the present invention, it is possible to increase the yield and to reduce the time. Solubilization is carried out through exposing, to the outside of a membrane protein, a part of the membrane protein integrated into a lipid membrane. This may pose the risk of decreasing homogeneity. According to the production method in accordance with an embodiment of the present invention, however, the solubilization is not carried out. This allows homogeneous membrane proteins to be obtained. In addition, correct folding can be maintained without dissociating lipids binding to a membrane protein with a weak binding force. This allows to original function to be correctly fulfilled. Therefore, the present invention can be particularly useful in, for example, crystallography analysis of membrane proteins, drug screening in which membrane proteins are targets, industrial production of membrane proteins, and antibody drug development (in which membrane proteins are used as antigens), all of which require a large amount of membrane proteins having excellent quality (such as more correct folding, more correct functions, high purity, and high homogeneity).

A membrane protein which has been collected can be used in the purifying step. This makes it possible to remove unnecessary components contained in the supernatant of the centrifugate, and therefore allows for an increase in purity. The purification can be carried out by, for example, column chromatography such as tag affinity column chromatography or size exclusion column chromatography. It is also possible to use a magnetic nanoparticle technique such as a technique in which magnetic beads are used.

In a case where a purification tag is added to a membrane protein, it is possible to include the step of cutting off the purification tag. Cutting off the purification tag allows the membrane protein to have a more correct tertiary structure.

[Use and Application of Membrane Protein]

A membrane protein produced by the production method in accordance with an embodiment of the present invention can have excellent quality as described above. The membrane protein produced by the production method in accordance with an embodiment of the present invention can have activity while being enclosed in a lipid-detergent assembly. Therefore, an embodiment of the present invention provides a composition containing a membrane protein which is enclosed in a lipid-detergent assembly.

The production method in accordance with an embodiment of the present invention is useful in preparation of a large amount of membrane proteins which (i) have a structure and activity that function in a living body and (ii) are stabilized. The synthesized membrane protein can be used as-is for a study of functional analysis and a study of structural analysis. The study of functional analysis can be used to determine an activity of the membrane protein by detecting mass transportation via a lipid bilayer membrane, and a binding with a ligand. The technique for functional analysis can be used for high-throughput screening which employs enzyme activity of a receptor protein or its connectivity to a ligand as an indicator. For example, a substance acting on a receptor protein is identified by using a peptide, a protein or a combinatorial library of compounds. In order to demonstrate a binding of a specific ligand which binds to GPCR or identify an inhibitor and competitor thereof, various ligand molecules can be labeled with radioisotope, fluorescent substance, luminescent compound and the like to analyze a binding with a receptor protein.

The study of structural analysis of the membrane protein can be carried out by, but not restricted to, X-ray crystallography analysis, nuclear magnetic resonance (NMR) analysis, small-angle X-ray scattering (SAXS), scanning probe microscope (SPM), atomic force microscopy (AFT) and the like. Crystallization for carrying out X-ray diffraction is possible by use of a lipid-detergent mixed proteomicelle or by carrying out further purification. Various methods have been also reported for crystallizing a receptor protein while the protein is present in phospholipid bilayer membrane (see, for example, the literature: Japanese Patent Application Publication, Tokukai, No. 2006-219401). Information on the structure of the membrane protein thus obtained can be used for, for example, drug design.

A membrane protein produced by the production method in accordance with an embodiment of the present invention can be used as an antigen in production of an antibody drug. In a case where (i) the membrane protein is used as an antigen while being integrated into a lipid membrane and (ii) the membrane protein is applied to a living body, it is possible to obtain an antibodies having a greater effect because the membrane protein is more correctly folded. In addition, the membrane protein produced by the production method in accordance with an embodiment of the present invention can be used for screening of such an antibody.

In addition, the membrane protein produced by the production method in accordance with an embodiment of the present invention is highly pure and contains few impurities. This makes it possible to obtain highly reliable results in drug search with use of libraries.

In addition, in another embodiment of the present invention, a viral protein or a tumor antigen can be expressed as a membrane protein, and an immunogenic composition containing it can be used as a component of vaccine. Examples of the viral protein encompass gp120 of human immunodeficiency virus, envelope glycoprotein of herpes simplex virus, spike protein of SARS virus, and hemagglutinin of influenza virus. An antigen which aids immune response includes a pathogen such as bacteria, and a membrane protein on the surface of a tumor cell.

The following description will provide Examples to more specifically describe embodiments of the present invention. Needless to say, the present invention is not limited to Examples provided below, but details of the present invention can be realized in various manners. Further, the present invention is not limited to the embodiments described above, and it may be varied in various ways within the scope of the appended claims. Thus, an embodiment based on a combination of technical means disclosed in different embodiments is encompassed in the technical scope of the present invention. Furthermore, all of the publications and patents cited in the present specification are incorporated herein by reference in their entirety.

EXAMPLES

The following description will discuss Examples and Comparative Examples to further describe the present invention. However, the present invention is not limited to these Examples or Comparative Examples.

Note that the reagents used in Examples were obtained the sources describe below. Digitonin was purchased from Wako Pure Chemical Industries, Ltd. Cholesteryl hemisuccinate (CHS) and most of the detergents were purchased from Anatrace. The following were purchased from Sigma-Aldrich: Brij-35, Brij-58, Brij-78, cholesterol, 3-sn-phosphatidic acid (PA), L-α-phosphatidylethanolamine (PE), L-α-phosphatidylinositol (PI), L-α-phosphatidyl-L-serine (PS), 3-[(3-cholamidopropyl)dimethylammonio]-1-propanesulfonate (CHAPS), and 7-diethylamino-3-(4-maleimidophenyl)-4-methylcoumarin (CPM). The following were purchased from Olbracht Serdary Research Laboratories: L-α-lysophosphatidylethanolamine (lyso-PE), L-α-lysophosphatidylserine (lyso-PS), and L-α-lysophosphatidylcholine lyso-PC. The following were purchased from Avanti Polar Lipids: 1,2-dimyristoyl-sn-glycero-3-phosphocholine (DMPC) and natural lipid. The following were purchased from Nikko Chemicals Co., Ltd.: pentaethylene glycol dodecyl ether ($C_{10}E_5$), octaethylene glycol decyl ether ($C_{10}E_8$), hexaethylene glycol dodecyl ether ($C_{12}E_6$), and octaethylene glycol dodecyl ether ($C_{12}E_8$). The following were purchased from Peptide Institute: intramolecular quenching fluorescent peptide probe Nma-Gly-Gly-Val-Val-Ile-Ala-Thr-Val-Lys(Dnp)-D-Arg-D-Arg-D-Arg-$NH_2$ (SEQ ID NO: 1), and GXGD protease inhibitor (Z-Leu-Leu)$_2$ ketone. The reagents and the tools for X-ray crystallography were purchased from Molecular Dimensions. Gradient polyacrylamide gel XVPANTERA Gel 10-20% was purchased from DRC. All of the other chemical substances were purchased from Nacalai Tesque.

Example 1

1. Selection of Kinds and Concentrations of Detergents

Example 1 shows a method of selecting the kinds and concentrations of detergents. Note that a preferable detergent concentration obtained by the selection method indicates a range of concentrations at which a lipid-detergent mixed micelle does not grow so that a lipid membrane is prevented from being stably formed.

(Example of Human γ-Secretase Complex)

Figure 5:
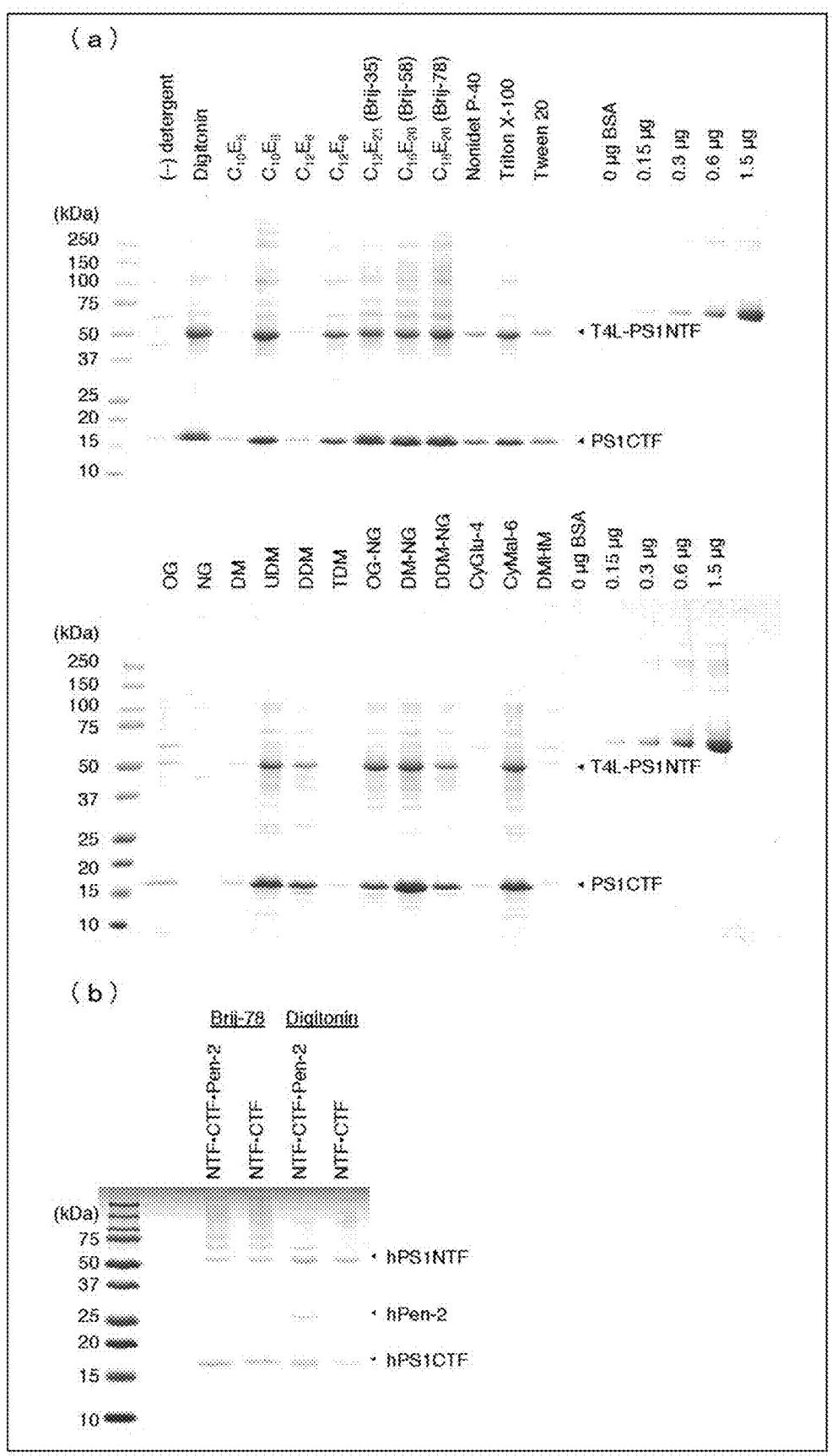
FIG. 5 is a view illustrating production of constituent elements of human γ-secretase in accordance with an embodiment of the present invention. (a) of FIG. 5 shows SDS-PAGE images of T4L-PS1NTF-PS1CTF complexes produced in the presence of various kinds of detergents. T4L-PS1NTF protein and PS1CTF protein were co-purified by tag affinity chromatography (in a 50 mM Tris-HCl buffer solution (pH 7.0) containing 0.05% β-DDM, 0.002% CHS, and 400 mM NaCl) with use of FLAG tag of (added to) a C-terminus of PS1CTF. (b) of FIG. 5 shows a SDS-PAGE image of T4L-PS1NTF-PS1CTF complex and T4L-PS1NTF-PS1CTF-Pen-2 complex which were produced by the method in accordance with an embodiment of the present invention in the presence of Brij-78 or digitonin and then purified with use of FLAG tag-added PS1CTF by the method similar to that of (a) of FIG. 5. $C_{10}E_5$, pentaethylene glycol dodecyl ether; $C_{10}E_8$, octaethylene glycol decyl ether; $C_{12}E_6$, hexaethylene glycol dodecyl ether; $C_{12}E_8$, octaethylene glycol dodecyl ether; OG, n-octyl-β-D-glucopyranoside; NG, n-nonyl-β-D-glucopyranoside; DM, n-decyl-β-D-maltopyranoside; UDM, n-undecyl-β-D-maltopyranoside; DDM, n-dodecyl-β-D-maltopyranoside; TDM, n-tridecyl-β-D-maltopyranoside; OG-NG, octyl glucose neopentyl glycol; DM-NG, decyl maltose neopentyl glycol; DDM-NG, dodecyl maltose neopentyl glycol; CyGlu-4, 4-cyclohexyl-1-butyl-β-D-glucopyranoside; CyMal-6, 6-cyclohexyl-1-hexyl-β-D-maltopyranoside; DMHM, 2,6-dimethyl-4-heptyl-β-D-maltopyranoside; BSA, bovine serum albumin.

A human γ-secretase complex is an intramembranous protease from which amyloid-β peptide relative to Alzheimer's disease is generated (Reference Literature 6). This huge membrane protein complex (approximately 170 kDa) is made of 4 subunits. A 9-transmembrane presenilin-1 (PS1) catalytic subunit is considered to interact with a 2-transmembrane presenilin promoting protein 2 (Pen-2) (Reference Literature 7). In the present invention, PS1NTF and PS1CTF were coexpressed under various detergent conditions to form a PS1NTF-PS1CTF complex. Then, the PS1NTF-PS1CTF complex was tested. As a result, several preferable detergent conditions were identified ((a) of FIG. 5). Furthermore, under these preferable detergent conditions, PS1NTF, PS1CTF, and hPen-2 of the present invention were coexpressed. This formed a PS1NTF-PS1CTF-Pen-2 complex ((b) of FIG. 5).

(Example of Human Claudin Family Protein)

Figure 6:
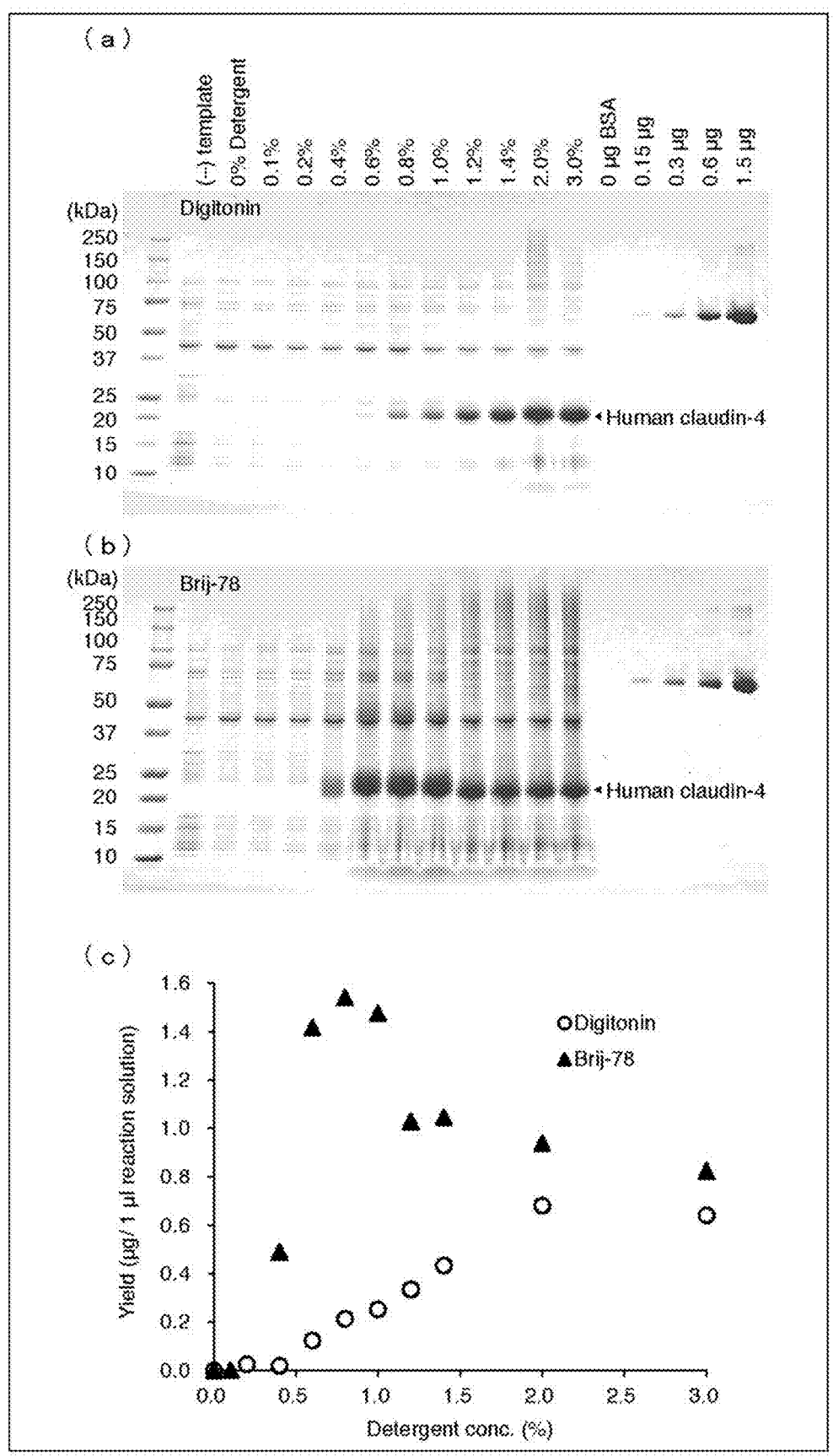
FIG. 6 is a view illustrating search for detergent concentration conditions of human claudin-4 in accordance with an embodiment of the present invention.
Figure 9:
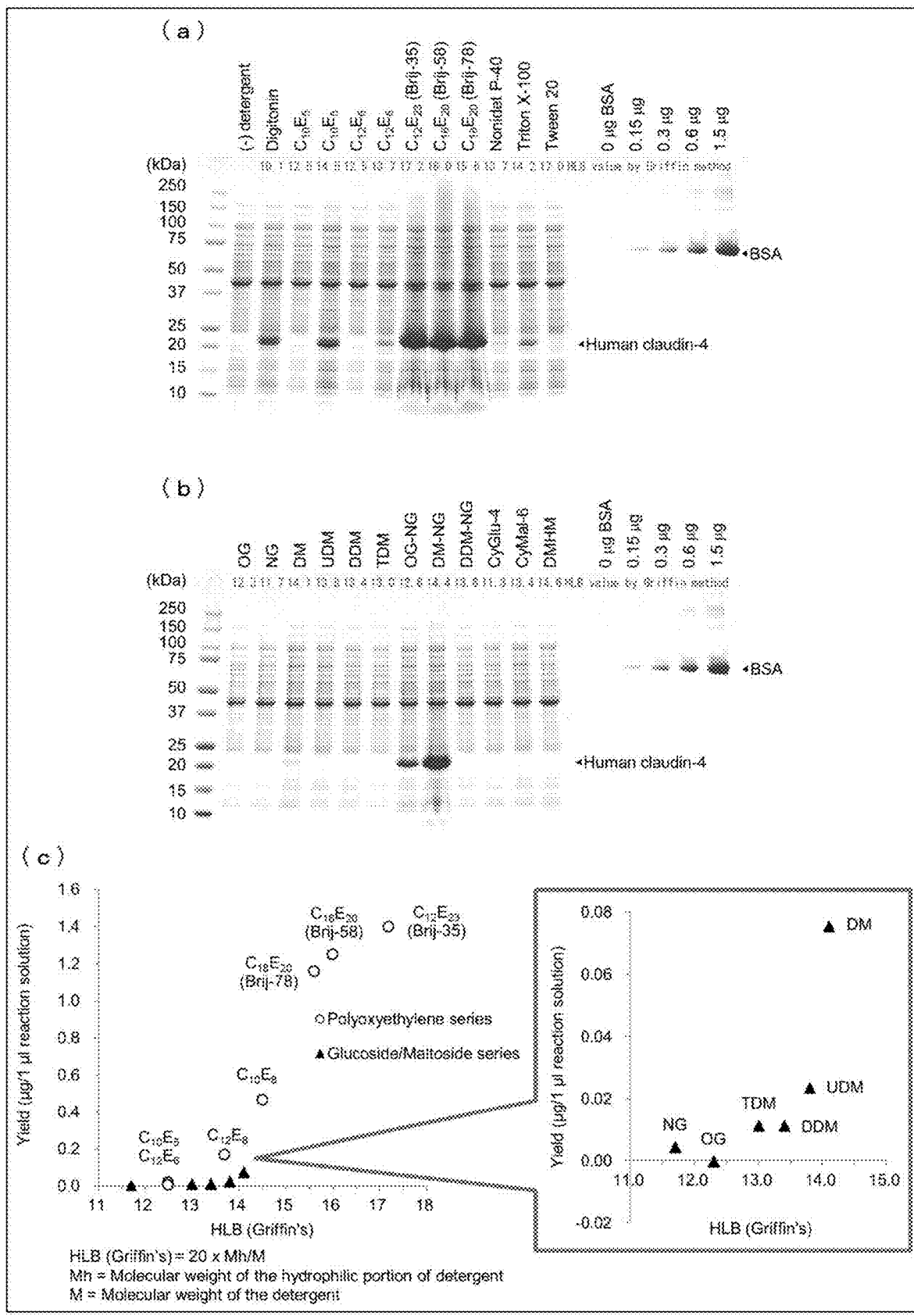
FIG. 9 is a view illustrating production of human claudin-4 in accordance with an embodiment of the present invention. (a) of FIG. 9 shows a SDS-PAGE image of human claudin-4 produced in an embodiment of the present invention in the presence of various kinds of nonionic detergents. The human claudin-4 was purified by affinity chromatography (in a 50 mM Tris-HCl buffer solution (pH 7.0) containing 0.05% β-DDM, 0.002% CHS, and 400 mM NaCl) with use of a native histidine tag added to an N-terminus of the human claudin-4. (b) of FIG. 9 is a view in which the strengths of the bands of the human claudin-4 in (a) of FIG. 9 was plotted with respect to HLB values of the nonionic detergents. The strengths of the bands were measured with use of Image J (http://imagej.nih.gov/ij/), and the amounts of proteins were estimated from the calibration curve with the BSA as a standard. The HLB value of each nonionic detergent was calculated by the Griffin method (HLB value=20×sum total of formula weights of hydrophilic portion/molecular weight) Note that "HLB" stands for Hydrophile-Lipophile Balance.

A human claudin family 4-transmembrane protein is a main constituent element of a tight junction strand, and contributes to paracellular permeability and a barrier function. In Example 1, a human claudin family 4-transmembrane protein in accordance with an embodiment of the present invention was expressed, and various detergents were searched (FIG. 9). Based on the results, a human claudin-4 protein was produced by the method in accordance with an embodiment of the present invention in the presence of digitonin ((a) of FIG. 6) and Brij-78 ((b) of FIG. 6) which had high yields. Then, purification was carried out by tag affinity chromatography (in 50 mM Tris-HCl buffer solution (pH 7.0) containing 0.05% β-DDM, 0.002% CHS, and 400 mM NaCl). Then, a detergent concentration which was preferable for synthesis was selected ((c) of FIG. 6).

(Example of Transporter A)

Figure 12:
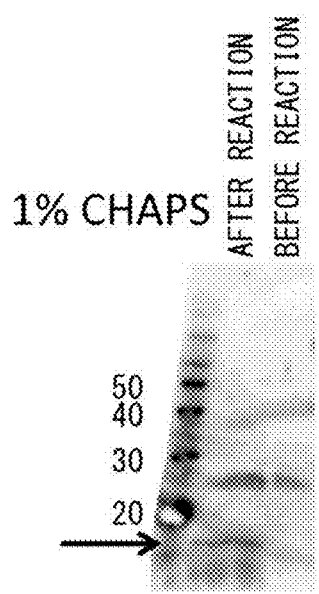
FIG. 12 is a view illustrating another example of the present invention.

Example 1 demonstrates that a membrane protein can be synthesized even in a case where an ionic detergent is used. Under the conditions where a mixture of an ionic detergent (1% CHAPS) and egg PC (6.7 mg/mL) was added, a transporter A was produced by the method in accordance with an embodiment of the present invention over 4 hours. Synthesized solutions before and after the reaction were each fractionated by 100,000 g centrifugation and subjected to SDS-PAGE. Then, a transporter A having an N11 tag at an N-terminus was analyzed by Western blotting in which HisProbe was used. The arrow in FIG. 12 indicates the band (approximately 15 kDa) of the synthesized transporter A.

(Example of Membrane Protein Synthesis by Combination of Detergents)

Figure 13:
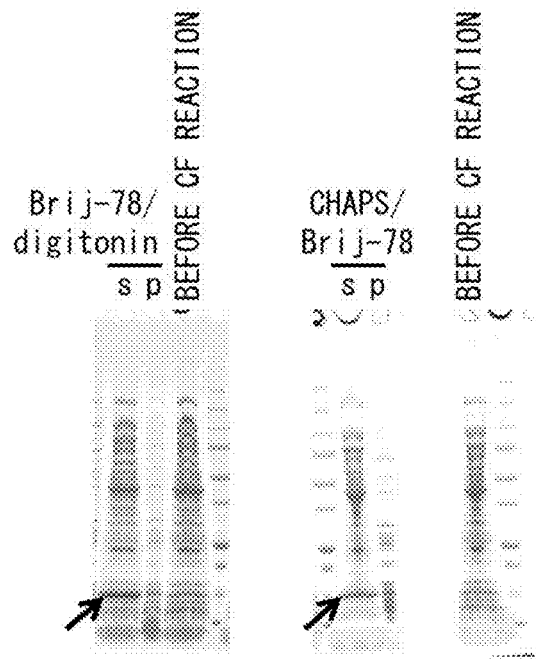
FIG. 13 is a view illustrating yet another example of the present invention.

Under the conditions where a mixture of egg PC (6.7 mg/mL) and a detergent ((i) 0.5% Brij-78 and (ii) 0.5% digitonin or 0.5% CHAPS) was added, a transporter A was produced by the method in accordance with an embodiment of the present invention over 4 hours. The reaction solution was fractionated by centrifugation (100,000 g, 15 minutes). The supernatant fraction and the precipitate fraction were analyzed by SDS-PAGE. The arrow in FIG. 13 indicates the band of the synthesized transporter A.

Assume a case where a bicelle is formed by use of (i) a ratio (q value) between a lipid selected from limited kinds of lipids and a detergent or (ii) a q value and a total lipid concentration ($C_L$ value) of the long-chain lipid concentration and the detergent concentration. In this case, unlike Example 1 of the present invention, it is impossible to narrow down combinations of lipids and detergents to a combination(s) which is/are suited for a target membrane protein, by searching for a proper detergent as demonstrated in Example 1 and by searching for proper lipids as demonstrated in Examples below.

2. Selection of Suitable Lipid Conditions

It is known that depending on the kind of membrane protein, there are membrane proteins which may require a plurality of kinds of specific lipids for the sake of structural stability and correct function (Non-Patent Literature 5, Reference Literature 1, and Reference Literature 2). In Example 1, a method of selecting suitable lipid conditions will be discussed.

(Method of Searching for Lipid Concentration: Example of Human Claudin Family Protein)

Figure 3:
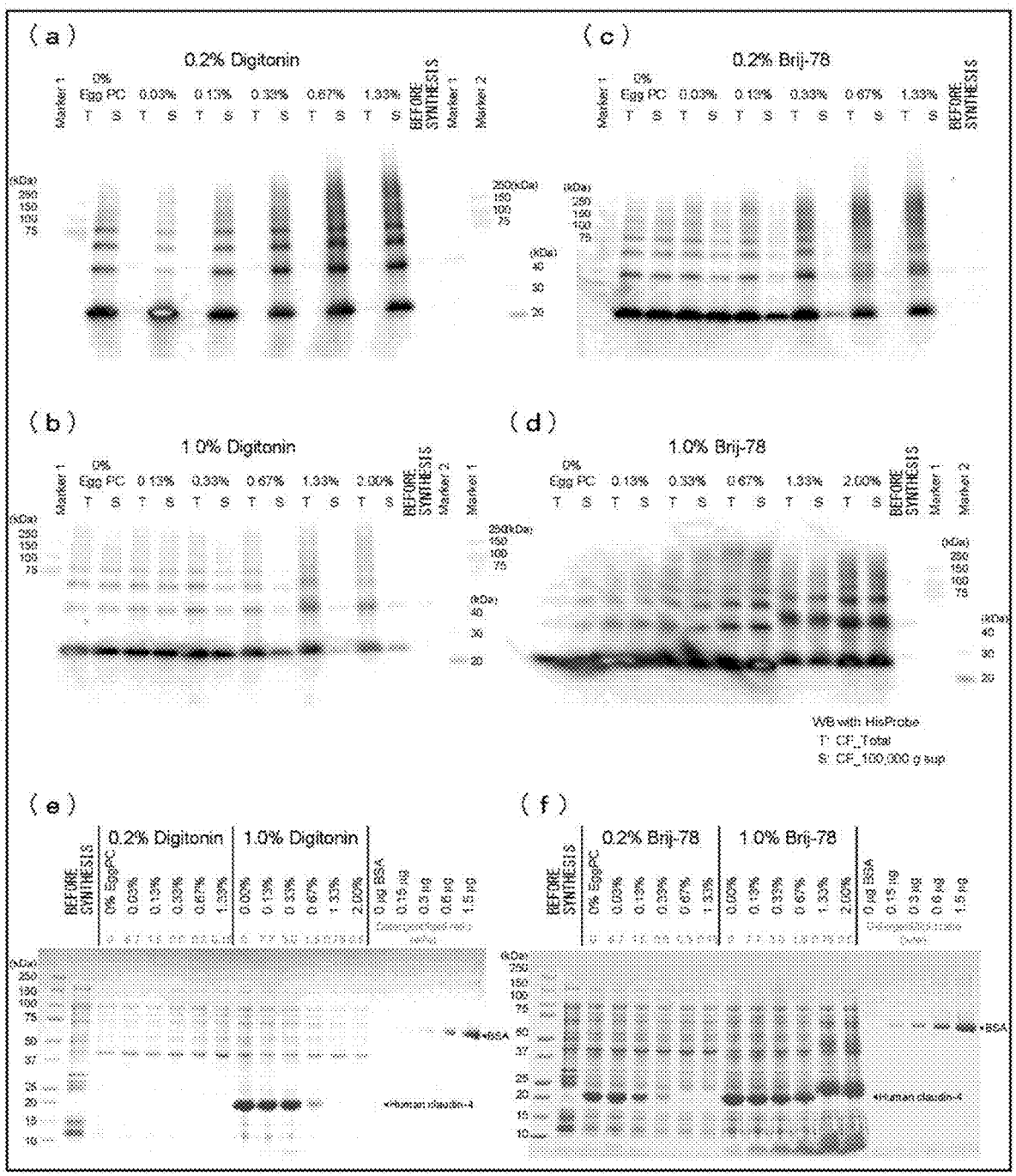
FIG. 3 is a view illustrating study of lipid concentrations in accordance with an embodiment of the present invention.

Based on the results of the detergent search in Example 1-1., egg PC concentrations under each of the detergent conditions in synthesis of human claudin-4 in accordance with an embodiment of the present invention were studied with use of (i) 1% digitonin and 1% Brij-78 which had high yields and (ii) 0.2% digitonin and 0.2% Brij-78 which had low yields and which served as controls (FIG. 3). The reaction solution 5 hours after the synthesis reaction was fractionated by 100,000 g centrifugation. For the reaction solution (T) before the centrifugation and fractionation and the 100,000 g supernatant fraction (S), a human claudin-4 having an N11 tag at an N-terminus was analyzed by Western blotting with use of HisProbe. (e) of FIG. 3 illustrates a gel image showing the analysis of human claudin-4 by SDS-PAGE and CBB staining after purifying, with Ni-sepharose (GE), the human claudin-4 contained in 100,000 g supernatant fractions under the digitonin conditions (a) and (b). The black arrowhead indicates the band of the human claudin-4. The ratio (weight ratio) between the detergent and the lipid in the synthesis reaction solution is also illustrated. As with (e) of FIG. 3, (f) of FIG. 3 illustrates a SDS-PAGE gel image showing the analysis after purifying the human claudin-4 contained in 100,000 g supernatant fractions under Brij-78 conditions (c) and (d).

(Method of Searching for Lipid Concentration: Example of Transporter A)

Figure 14:
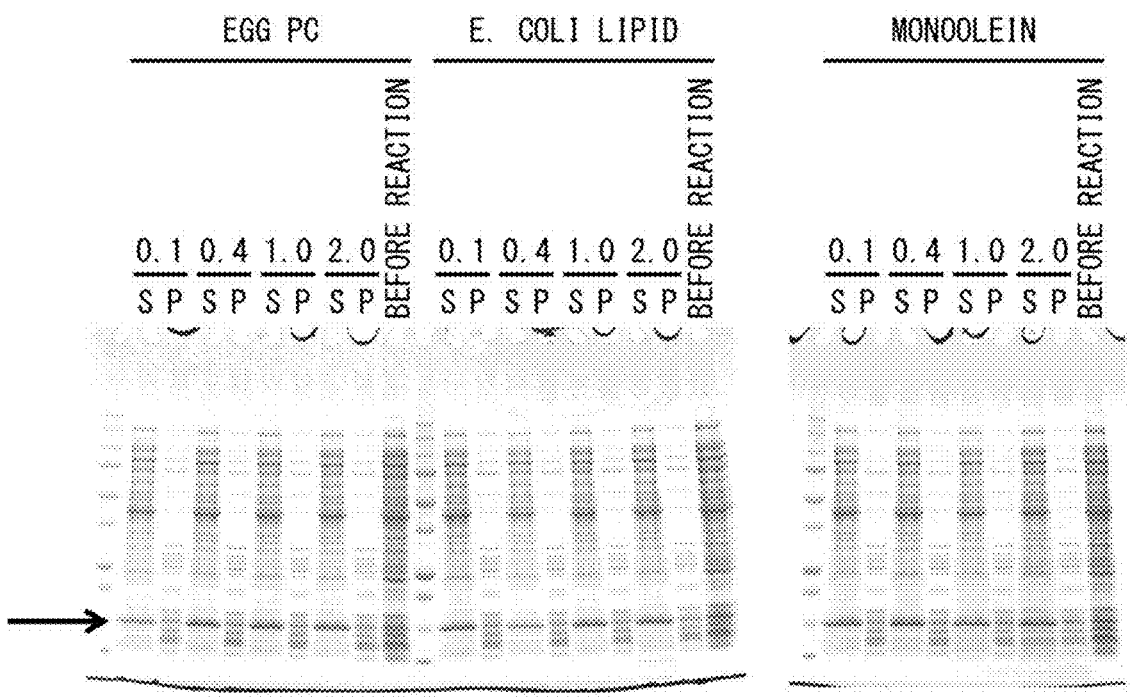
FIG. 14 is a view illustrating yet another example of the present invention.

To the reaction solution, the following were added: (i) 1 mg/mL to 20 mg/mL egg PC, (ii) *E. coli* lipid or monoolein, and (iii) a detergent (1% Brij-78). Then, a synthesis reaction was made over 3 hours. The reaction solution was fractionated by centrifugation (100,000 g, 15 minutes). The supernatant fraction and the precipitate fraction were analyzed by SDS-PAGE. The arrow in FIG. 14 indicates the band of the synthesized transporter A.

(Method of Searching for Suitable Lipid: Example of Human Glucosylceramide Synthase (GlcT))

Figure 2:
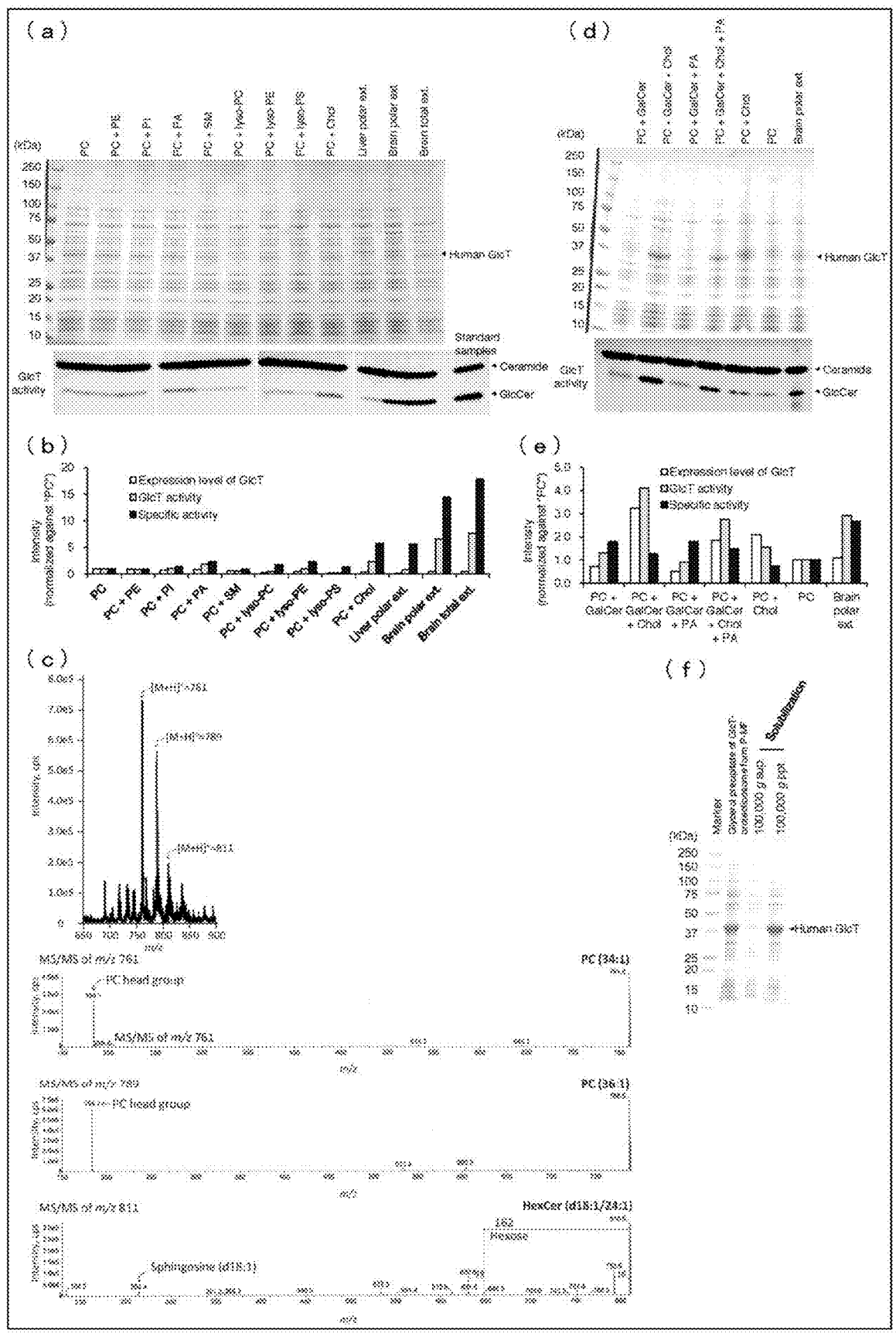
FIG. 2 is a view illustrating improvements in expression level and specific activity of human GlcT as a result of search for lipid under cell-free synthesis conditions. PC is phosphatidylcholine; PE is phosphatidylethanolamine; PI is phosphatidylinositol; PA is phosphatidic acid; SM is sphingomyelin; lyso-PC is lysophosphatidylcholine; lyso-PE is lysophosphatidylethanolamine; lyso-PS is lysophosphatidylserine; Chol is cholesterol; GalCer is galactosylceramide; and GlcCer is glucosylceramide.

Glucosylceramide synthase (GlcT) is an estimated 3-transmembrane protein serving as the first enzyme in biosynthesis of glycolipid (Reference Literature 4) With use of the present sample, searches for various lipids were conducted with effects on GlcT generation level and enzyme activity (Reference Literature 5) as indicators ((a) of FIG. 2). Egg PC is typically used as lipids in a cell-free protein synthesis system. Glucosylceramide is a kind of sphingoglycolipid. It is known that plenty of sphingoglycolipid is contained in brain tissues. In addition, many sphingoglycolipids are synthesized with glucosylceramide as a starting material. Therefore, in Example 1, searches for lipids suitable for GlcT were conducted among porcine brain-derived lipid mixtures. In comparison with egg PC ("PC" lane in (a) and (b) of FIG. 2), specific activity of GlcT was remarkably increased in porcine brain-derived lipid mixtures. In addition, even in a case where PA or cholesterol (5%) was added to egg PC (95%), the degree of increase in specific activity was small. Meanwhile, synthesis was not observed in a case where the synthesis was attempted in the presence of (i) a porcine liver lipid mixture or lyso-PC (5%) and (ii) egg PC (95%). Next, the identification of the kinds of lipids that contribute to an increase in specific activity was attempted by carrying out MS/MS analysis on binding lipids in purified samples of GlcT synthesized with use of porcine brain lipid mixtures. As a result, hexosylceramide was detected in addition to PC (34:1) and PC (36:1) which are main lipids ((c) of FIG. 2). Hexosylceramide was presumed as galactosylceramide (GalCer) which is main hexosylceramide in a brain lipid mixture. Example 6 shows the results of producing GlcT with use of GalCer. In a case where it is difficult to predict lipid candidates in advance, suitable lipids can be selected for (bound to) a target membrane protein with use of lipid mixtures containing various kinds of lipids as demonstrated in Example 6. There has been no report on a method in which lipids that have biological activity and that are necessary for forming a correct tertiary structure are thus synthesized while the lipids are selected for a membrane protein.

(Method of Searching for Suitable Lipid: Example of Human Claudin-4-C-CPE Complex)

It is important to select a lipid essential for the formation of a protein complex. Example 1 demonstrates a method of identifying a lipid which binds to a claudin-4-C-CPE complex to improve stability.

Claudin-4 was synthesized with use of (i) egg PC and cholesterol, (ii) PE (phosphatidylethanolamine) and egg PC, and (iii) porcine liver and egg PC. While the N11 tag of the N-terminus of each claudin-4 was being dialyzed with respect to a dialysis buffer A (50 mM Tris-HCl buffer solution (pH 7.0) containing 0.05% B-DDM, 0.002% CHS, and 400 mM NaCl), the N11 tag was cut by digestion at 4° C. overnight with use of His tag-added TEV protease. N11 tag fragment and His tag-added TEV protease were removed by Reverse IMAC, untagged claudin-4 was collected from flow-through fractions and wash fractions. The claudin-4 thus obtained was mixed with overdose purified C-CPE. The resulting mixture was incubated at 4° C. for 1 hour, so that a claudin-4-C-CPE complex was formed. The complex was (i) adsorbed to Ni-Sepharose resin by the N11 tag, (ii) washed with a washing buffer B (50 mM Tris-HCl buffer solution (pH 8.0) containing 0.025% $C_{12}E_8$, 0.002% CHS, and 150 mM NaCl), and (iii) eluted with an elution buffer B (50 mM Tris-HCl buffer solution (pH 8.0) containing 0.025% $C_{12}E_8$, 0.002% CHS, 500 mM imidazole, and 150 mM NaCl). After purification of the complex, the N11 tag of C-CPE was cut by digestion at 4° C. overnight with use of TEV protease while the elution buffer B was dialyzed with respect to a dialysis buffer B (50 mM Tris-HCl buffer solution (pH 8.0) containing 0.025% $C_{12}E_8$, 0.002% CHS, and 150 mM NaCl). N11 tag fragments were removed in the foregoing manner. Lastly, in a running buffer (50 mM Tris-HCl buffer solution (pH 8.0) containing 0.025% $C_{12}E_8$ and 150 mM NaCl), the sample was fractionated with use of a gel filtration column (Superdex 200 10/300) so as to be separated into a monodisperse peak of the protein complex. Note that the C-CPE was prepared by (i) fusing N11 tag and FLAG tag, TEV protease recognition site and GSSGSSG (SEQ ID NO: 2) linker sequence with the N-terminus and (ii) carrying out synthesis in a cell-free protein synthesis system in the absence of a detergent and lipids. From 30 µg of a purified claudin-4-C-CPE complex, lipids were extracted with use of chloroform/methanol (2:1 (v/v)), and the lipid extracts were spotted on a Silica Gel 60 TLC plate (manufactured by Merck). The lipids were separated with a mobile phase containing chloroform, methanol, n-hexane, diethyl ether, acetate, and water (75:45:80:20:13:6 (v/v)), and were detected with use of a phosphomolybdic acid reagent (manufactured by Merck).

Figure 4:
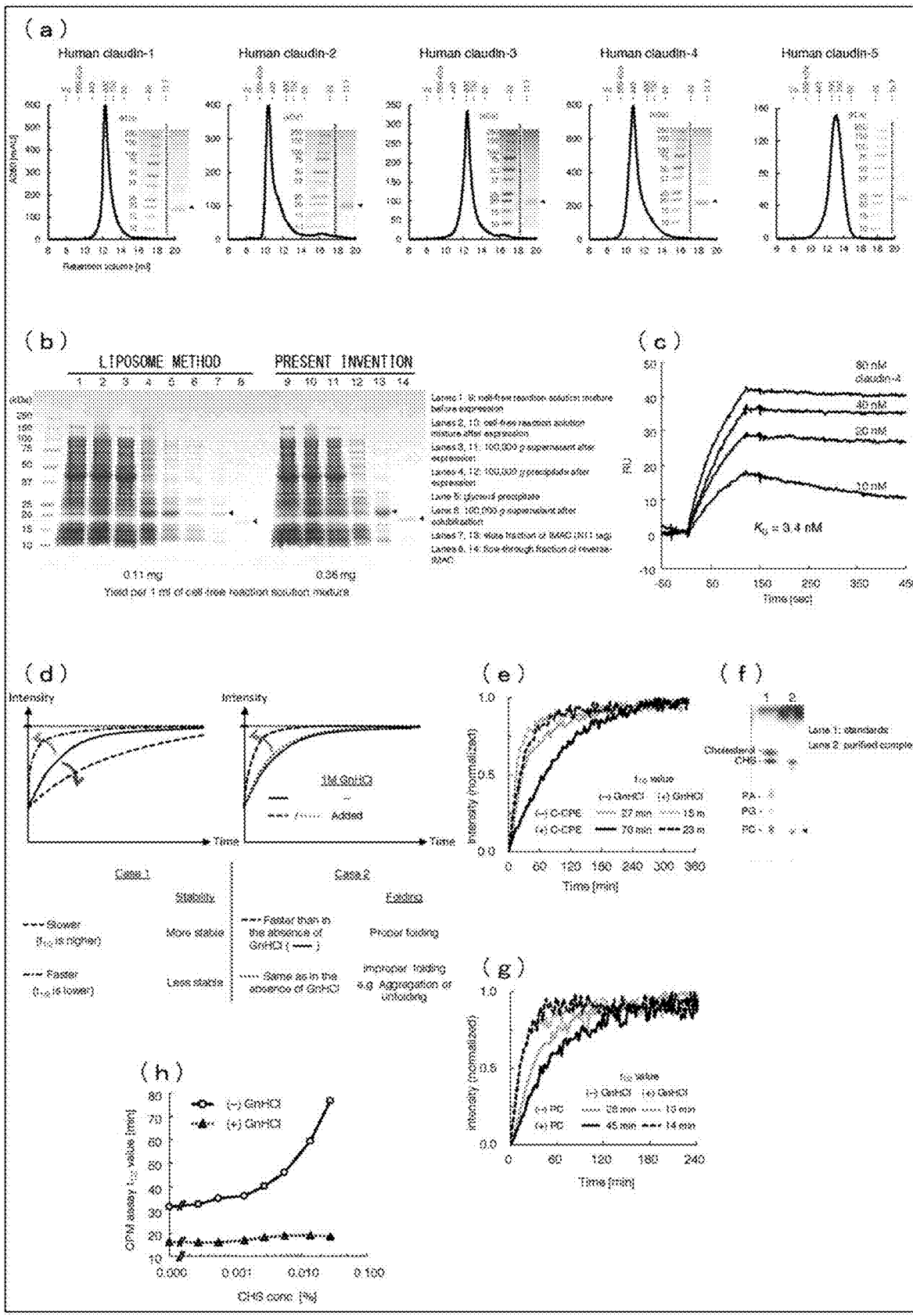
FIG. 4 is a view illustrating characteristics of human claudin produced in an embodiment of the present invention. (a) of FIG. 4 shows an SEC elution profile of human claudin produced in an embodiment of the present invention. SEC fractions of the peaks were analyzed by SDS-PAGE and CBB staining. (b) of FIG. 4 shows comparisons between characteristics of claudin-4 produced by the liposome method (lanes 1 through 8) and characteristics of claudin-4 produced by the method in accordance with an embodiment of the present invention (lanes 9 through 14). Fractions in the purifying step were analyzed by SDS-PAGE and CBB staining. (c) of FIG. 4 shows binding analysis, by a surface plasmon resonance method, of claudin-4 synthesized in a cell-free system, with respect to GST tag-added C-CPE fixed to a sensor chip. (d) of FIG. 4 shows CPM assays of membrane proteins in the absence of and in the presence of 1 M guanidine-HCl (GuHC1). (e) of FIG. 4 shows the analysis, by CPM assay, of thermal stability of claudin-4 (gray) and claudin-4-C-CPE complex (black) at 40° C. in the absence of GnHC1 (solid line) and in the presence of GnHC1 (dotted line). (f) of FIG. 4 shows TLC analysis for detection of lipids binding to claudin-4 in purified claudin-4-C-CPE complex samples. (g) of FIG. 4 shows CPM assay for evaluating thermal stability effect of PC with respect to claudin-4-C-CPE complexes. (h) of FIG. 4 shows CPM assay for evaluating thermal stability effect of CHS with respect to claudin-4-C-CPE complexes. t1/2 values at respective concentrations in the absence of 1 M GnHC1 (white circles) and in the presence of 1 M GnHC1 (black triangles) were plotted in a graph.

As a result of TLC analysis, PC as a binding lipid was detected from a purified specimen of claudin-4-C-CPE complex ((g) of FIG. 4). Also with regard to cholesterol containing a large amount of membranous domains in which claudin-4 is localized, the stabilization effect on the claudin-4-C-CPE complex with use of CPM assay as in the case of PC. Then, the effects dependent on the amount of the cholesterol added were shown (see the white circles in (h) of FIG. 4). Therefore, in the cell-free synthesis and purification of claudin-4, suitable PC or cholesterol/CHS identified in Example 1 is added to the system.

Example 2

Example 2 demonstrates that a membrane protein can be synthesized under conditions where a detergent concentration is not particularly limited, provided that the detergent concentration is a concentration equal to or higher than a critical micelle concentration.

(Detergent Concentration: Examples in which Detergent Concentration is 1 Time to 3 Times as High as Critical Micelle Concentration)

Figure 15:
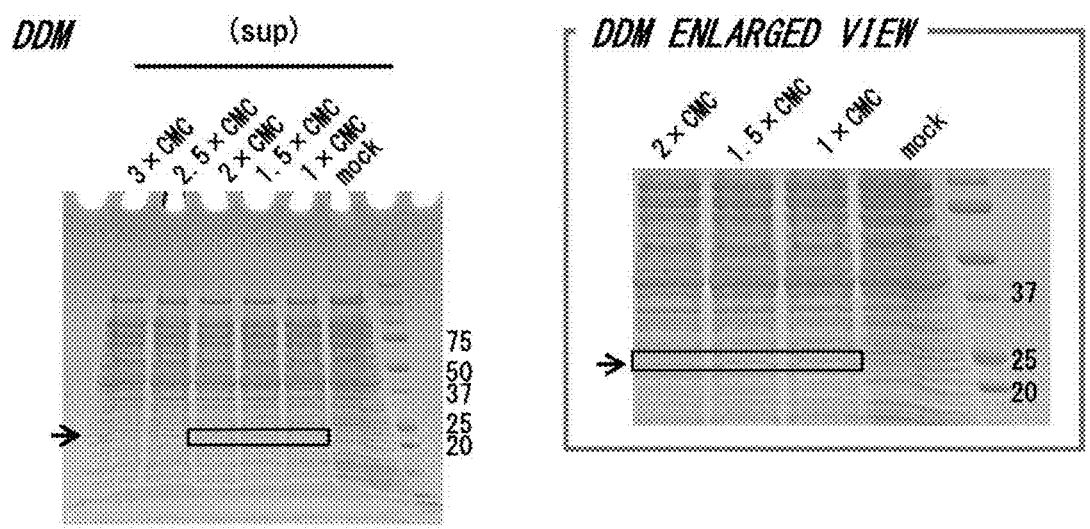
FIG. 15 is a view illustrating yet another example of the present invention.

A channel A, which is a membrane protein, was used to make a synthesis reaction for 5 hours. The reaction solution contained (i) porcine brain lipid at a final concentration of 4.3 mg/ml and (ii) DDM (1×CMC: 0.0087%, 1.5×CMC: 0.013%, 2×CMC: 0.017%, 2.5×CMC: 0.022%, and 3×CMC: 0.026%) serving as a detergent. The reaction solution was fractionated by centrifugation (100,000 g, 15 minutes) and analyzed with SDS-PAGE. The arrows in FIG. 15 indicate the band (approximately 22 kDa) of the channel A produced.

(Detergent Concentration: Examples in which Detergent Concentration is 3000 Times as High as Critical Micelle Concentration)

Figure 16:
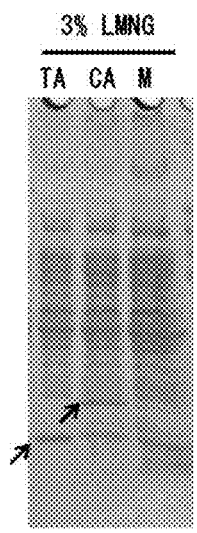
FIG. 16 is a view illustrating yet another example of the present invention.

The synthesis reaction was made for 4 hours. The reaction solution contained (i) porcine brain lipid at a final concentration of 4.3 mg/ml and (ii) a detergent (3% LMNG). The reaction solution was fractionated by centrifugation (100, 000 g, 15 minutes) and analyzed with SDS-PAGE. The arrows in FIG. 16 indicate the band of the membrane proteins produced (transporter A (TA), channel A (CA)) (M is Mock).

Example 3

Example 3 demonstrates that a membrane protein can be produced under conditions where a centrifugal force is not particularly limited during centrifugation.

Figure 17:
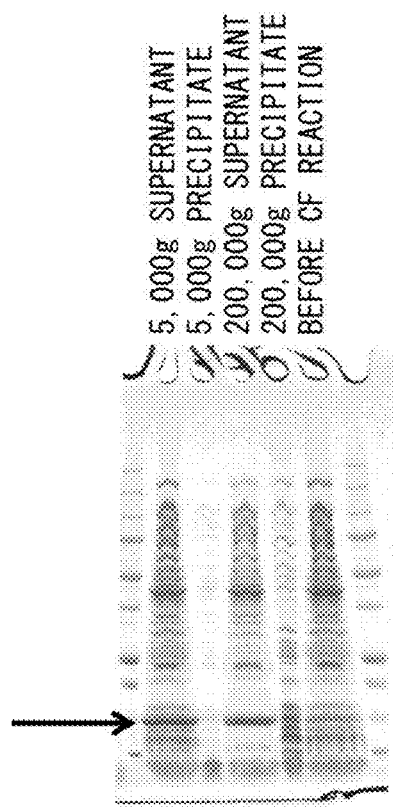
FIG. 17 is a view illustrating yet another example of the present invention.

Under the conditions where a mixture of egg PC (6.7 mg/mL) and 1% Brij-78 was added, a transporter A was produced by the method in accordance with an embodiment of the present invention over 4 hours. The reaction solution was fractionated at 5,000 g or 200,000 g for 15 minutes. The supernatant fraction and the precipitate fraction were analyzed by SDS-PAGE. The arrow in FIG. 17 indicates the band of the expressed transporter A.

Example 4

Example 4 demonstrates that a membrane protein can be produced only by carrying out a purifying step without centrifugation.

(Example of Purifying Step by Affinity Chromatography)

Figure 18:
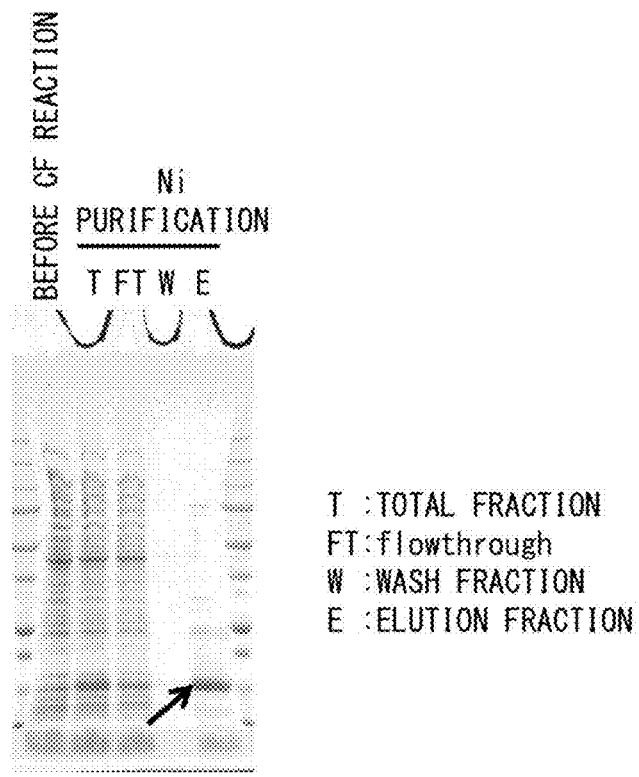
FIG. 18 is a view illustrating yet another example of the present invention.

Under the conditions where a mixture of egg PC (6.7 mg/mL) and 1% Brij-78 was added, a transporter A was produced by the method in accordance with an embodiment of the present invention over 4 hours. A gel image shows the analysis the transporter A by SDS-PAGE and CBB staining after purifying the transporter A with Ni-sepharose (GE) of the uncentrifuged reaction solution. The arrow in FIG. 18 indicates the band of the expressed transporter A.

(Example of Purifying Step by Magnetic Nanoparticle Technique)

Figure 19:
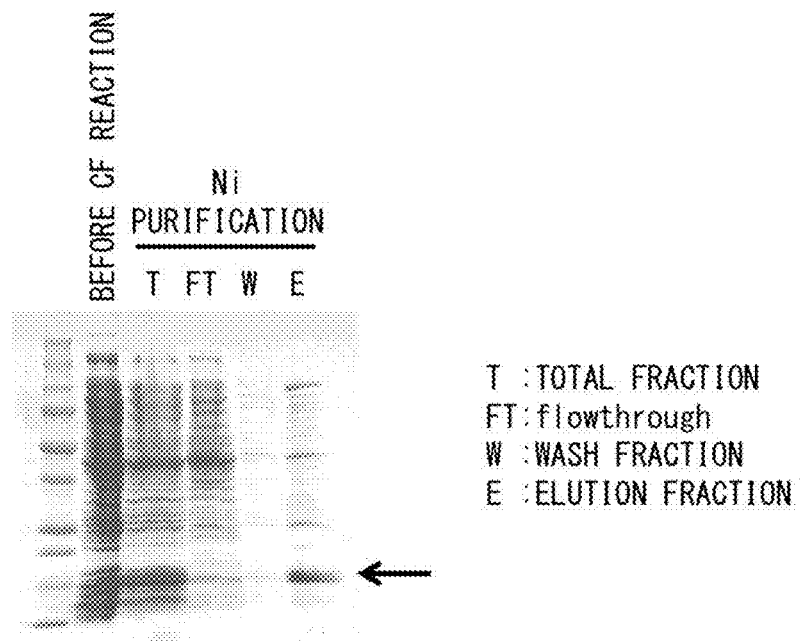
FIG. 19 is a view illustrating yet another example of the present invention.

Under the conditions where a mixture of egg PC (6.7 mg/mL) and 1% Brij-78 was added, a transporter A was produced by the method in accordance with an embodiment of the present invention over 4 hours. A gel image shows the analysis of the transporter A by SDS-PAGE and CBB staining after purifying the transporter A with His Mag Sepharose Ni (GE) of the uncentrifuged reaction solution. The arrow in FIG. 19 indicates the band of the expressed transporter A.

Example 5

Figure 20:
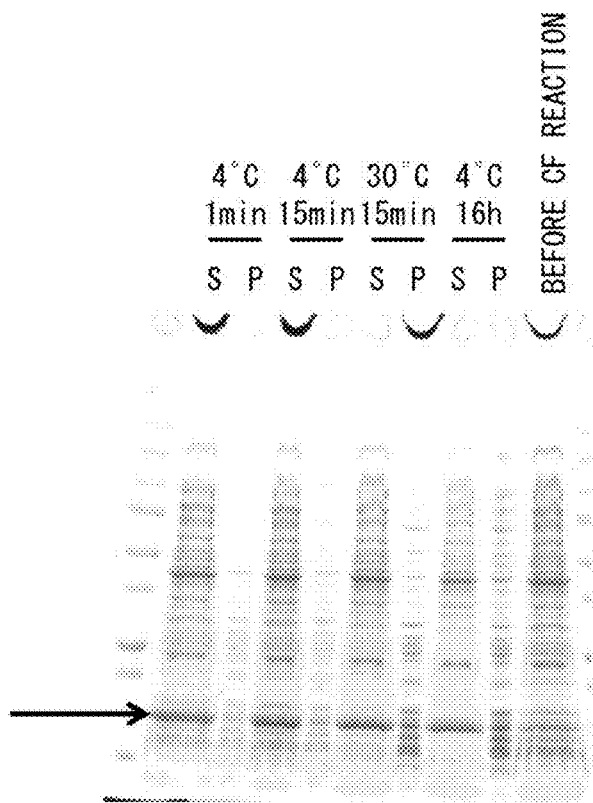
FIG. 20 is a view illustrating yet another example of the present invention.

Example 5 demonstrates that a membrane protein can be produced under conditions where neither a temperature during the centrifugation nor a period of the centrifugation is particularly limited. Under the conditions where a mixture of egg PC (6.7 mg/mL) and 1% Brij-78 was added, a transporter A was produced by the method in accordance with an embodiment of the present invention over 4 hours. The reaction solution was fractionated for 1 minute, 15 minutes, 16 hours (100,000 g, 4° C.), or 15 minutes (100,000 g, 30° C.). The supernatant fraction and the precipitate fraction were analyzed by SDS-PAGE. The arrow in FIG. 20 indicates the band of the expressed transporter A.

Example 6

(Synthesis of Human Claudin-4)

A human claudin-4 in accordance with an embodiment of the present invention was synthesized. The gene encoding the human claudin-4 (residue: 1 to 183) was subcloned except that a sequence encoding TEV protease recognition site and FLAG tag was added to the 3' terminus. A T4 phage lysozyme-claudin-4 fusion protein (T4L-claudin-4) was produced according to the known method (Reference Literature 8), and TEV site and FLAG tag were added to the C-terminus side. Under the conditions where a mixture of a lipid mixture (composed of cholesterol (5% (w/w)) and egg PC (95% (w/w))) at 6.7 mg/mL and digitonin at 10.0 mg/mL was added, claudin-4 and T4L-claudin-4 were produced by the method in accordance with an embodiment of the present invention at 30° C. over 5 hours. The sample labeled with selenium was produced as with a native protein except that methionine in the reaction solution and the supply solution was replaced with selenomethionine. The claudin-4 synthesized in this reaction solution was (i) collected in 100,000 g supernatant, (ii) adsorbed to Ni-Sepharose affinity resin, (iii) washed with a washing buffer A (50 mM Tris-HCl buffer solution (pH 7.0) containing 0.05% β-DDM, 0.002% CHS, 20 mM imidazole, and 400 mM NaCl), and then (iv) eluted with use of an elution buffer which is identical to the washing buffer A except 500 mM imidazole is contained.

(Results of Synthesis and Purification of 5 Kinds of Claudin Protein)

5 kinds of claudin proteins synthesized by the method above were purified by Ni affinity chromatography. As a result, all of the 5 claudin samples exhibited high synthesis levels, and it was revealed by SEC analysis that all of the 5 claudin samples were monodispersed with hardly any aggregation ((a) of FIG. 4). Therefore, Example 6 demonstrates that the method in accordance with an embodiment of the present invention is applicable to many of claudin family members which are difficult to prepare in a large amount.

Example 7

(Interaction Between Human Claudin-4 and *Clostridium perfringens* Enterotoxin (CPE))

Food-poisoning-inducing bacteria *Clostridium perfringens* secretes enterotoxin (CPE). CPE targets human claudin-4 with extremely high affinity (Reference Literature 9). In Example 7, surface plasmon resonance was used to measure the affinity of human claudin-4 with C-terminal fragment (C-CPE) composed of residues 185 to 319 containing a putative claudin-4 binding site. The measurement revealed that the $K_D$ value was 3.4 nM ((c) of FIG. 4). This value is substantially identical to the value obtained in a cell-based assay.

Example 8

(Analysis of Thermal Stability of Claudin-4 by CPM Assay)

Structural integrity and stability of a purified membrane protein are desirably evaluated by CPM assay. In this assay, the thermal denaturation of an analyte at 40° C. is monitored by the fluorescence of 7-diethylamino-3-(4-maleimidophenyl)-4-methylcoumarin (CPM) dye (which reacts with exposed cysteine residue (if present)). In a case where the $t_{1/2}$ value of the thermal denaturation at 40° C. is not less than 17 minutes, the membrane protein is considered sufficient stable (Reference Literature 3). Theoretically, a more stable membrane protein has a longer $t_{1/2}$ value. However, the inventors of the present invention found that strong aggregation of a membrane protein, which aggregation is derived from misfolding, leads to a longer $t_{1/2}$ value. Therefore, for the purpose of distinguishing between desired stability and undesirable aggregation, CPM assays of membrane proteins in the presence and absence of 1 M guanidine-HCl (GnHCl) were compared. A protein correctly folded exhibits a shorter $t_{1/2}$ value in the presence of 1 M GnHCl ((d) of FIG. 4, Case 1). Meanwhile, in the case of strong aggregation, such a difference is not shown ((d) of FIG. 4, Case 2). Therefore, with CPM assay, it is possible to finally evaluate (i) the status of purified samples and (ii) the effects of stabilizing factors of the purified samples.

Therefore, the structural integrity and stability of purified human claudin-4 were tested with CPM assay. The $t_{1/2}$ values of the claudin-4 in the absence of and in the presence of GnHCl at 40° C. were 27 minutes and 15 minutes, respectively (gray dotted lines in (e) of FIG. 4). This indicates that the samples synthesized by the present invention have sufficiently stable and integral structure. The $t_{1/2}$ values of the complex of claudin-4 and C-CPE in the absence of and in the presence of GnHCl were 70 minutes and 23 minutes, respectively (black dotted lines in (e) of FIG. 4). Furthermore, adding PC (which is suitable lipid identified in Example 1) to the sample led the $t_{1/2}$ value in the CPM assay to increase by 1.7 times (black dotted line in (g) of FIG. 4). The specific method will be described below.

CPM assay was carried out with a procedure obtained by improving the procedure of Hanson et al. (Reference Literature 2). Before the reaction started, 100 μL buffer solution (50 mM Tris-HCl buffer solution (pH 7.0 or 8.0) containing 0.05% β-DDM, 0.02% CHS, and 150 mM NaCl, and, as a denaturating agent, containing or not containing 0.2 M guanidine-HCl (GnHCl)) was placed in a 96-well black plate (manufactured by Nunc), and was maintained at 25° C. until the measurement started. The purified protein sample was diluted to 0.05 mg/mL with a reaction buffer, and 240 μL of the resulting protein sample was placed in another 96-well plate on ice. In blank wells, the same amount of reaction buffer was placed. 24 μL of 0.4 mg/mL CPM in the reaction buffer was added to each well, mixed through 10 times of pipetting, and incubated on ice for 15 minutes. A portion (100 μL) of the mixture was transferred to a well of the black plate, and then mixed through 10 times of pipetting. Immediately the measurement was started. The fluorescence, which is excited at 355 nm and emitted at 460 nm, is measured at 40° C. at intervals of 1 minute for 4 hours to 6 hours with use of ArvoX3 fluorophotometer (manufactured by PerkinElmer). A $t_{1/2}$ value, which is defined as a period during which CPM fluorescence intensity becomes half of the maximum value, was calculated from a linear region close to the $t_{1/2}$ value in each fluorescence intensity curve.

Example 9

(Crystallization and Structure Determination of Human Claudin-4-C-CPE Complex)

Figure 8:
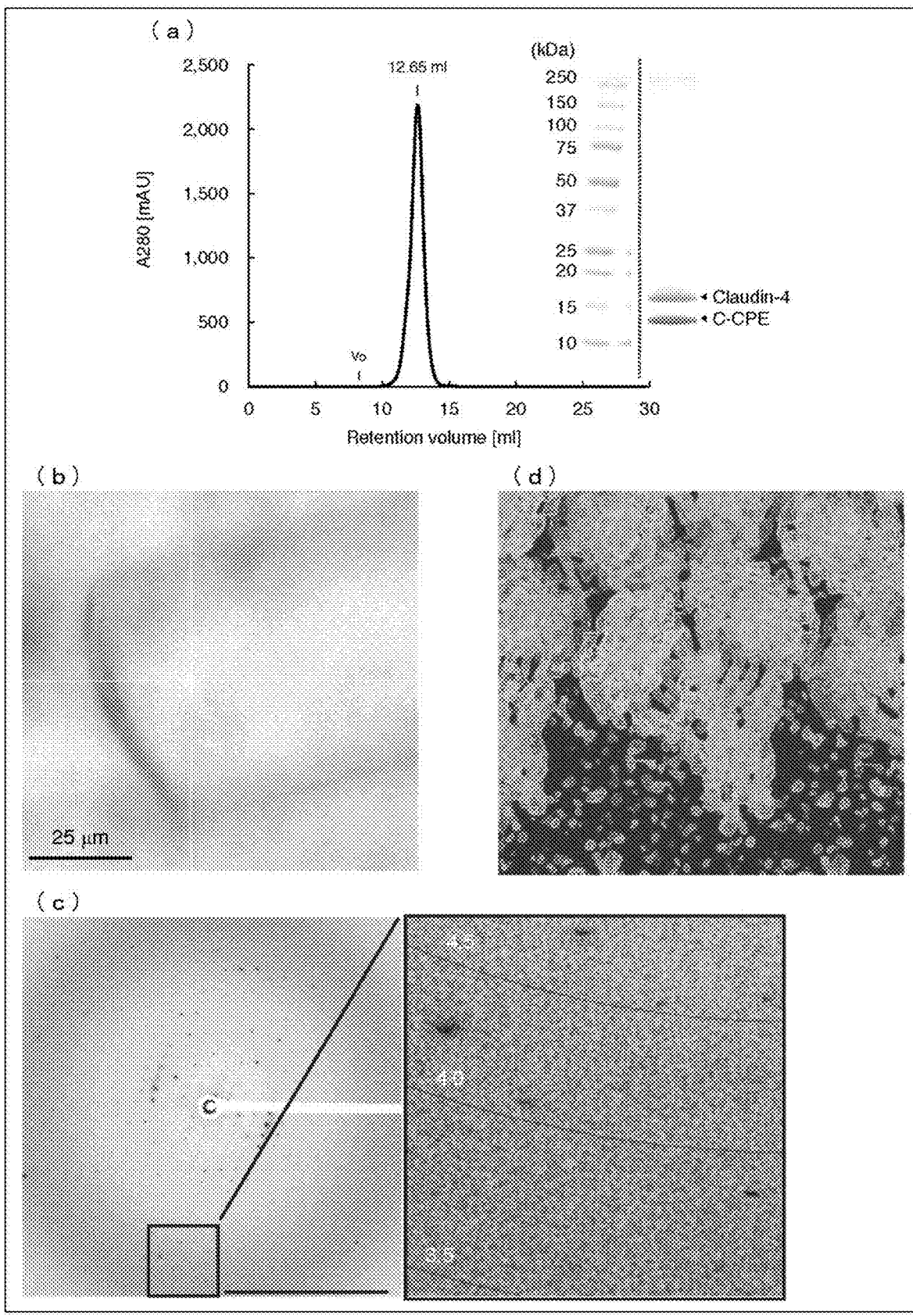
FIG. 8 is a view illustrating X-ray crystallography of human claudin-4-C-CPE complex. (a) of FIG. 8 shows SEC elution profile of human claudin-4-C-CPE complex. (b) of FIG. 8 shows a crystal of the human claudin-4-C-CPE complex. (c) of FIG. 8 shows a diffraction image collected from a crystal of the human claudin-4-C-CPE complex with use of BL32XU of SPring-8. (d) of FIG. 8 shows an electron density map of an initial phase of the human claudin-4-C-CPE complex at a resolution of 4.5 Å. This electron density map was used to produce COOT program (Reference Literature 14).

In Example 9, the high quality of the membrane protein synthesized in accordance with an embodiment of the present invention is verified by an example in which a crystal of a claudin-4-C-CPE complex was successfully obtained, which crystal causes diffraction at a resolution of approximately 4 Å ((a) through (c) of FIG. 8). The specific method will be described below.

A purified complex was incubated at 4° C. for 30 minutes together with egg PC in an amount of 0.05 mg with respect to 1 mg of protein. Then, the resulting product was incubated at 4° C. for 1 hour together with Biobeads SM2 (manufactured by Bio-Rad) in an amount of 25 µL per with respect to 1 mL of protein solution. The Biobeads were removed by filtering with use of a 0.22 µm filter (manufactured by Millipore). This sample was concentrated to approximately 20 mg/mL with use of an Amicon Ultra-4 filter including a 10,000-Da molecular weight cut-off (manufactured by Millipore). In addition, the crystallization was carried out with use of a T4L-claudin-4-C-CPE complex produced by a method similar to the method of producing the claudin-4-C-CPE complex demonstrated in Example 1.

The claudin-4-C-CPE complex and the T4L-claudin-4-C-CPE complex were crystallized by the same method. 6 mg/mL to 8 mg/mL protein samples before the treatment and concentrated protein samples were incubated in 3.6 mg/mL to 10.0 mg/mL lipid suspensions in 20 mM Tris-HCl buffer solution (ph 7.0) containing 0.75% $C_{12}E_8$ and 10 mM reduced glutathione. In so doing, cholesterol/sphingomyelin/egg PC (7.5:2.5:90 (w/w)) was used as a claudin-4-C-CPE complex, and egg PC was used as a T4L-claudin-4-C-CPE complex. After incubating on ice for 1 hour, the samples were each mixed with a reservoir solution in an equivalent amount. The reservoir solution of the claudin-4-C-CPE complex was a 75 mM MES-NaOH buffer solution (pH 5.5 to 6.0) containing 20% (w/v) PEG3350, 5% to 7% (v/v) 2-methyl-2,4-pentanediol, 0.002% (w/v) $NaN_3$, 0.0005% (w/v) 2,6-di-t-butyl-β-cresol, and 150 mM NaCl. The reservoir solution of the T4L-claudin-4-C-CPE complex was 75 mM MES-NaOH buffer solution (ph 5.0 to 5.5) containing 20% (w/v) PEG3350, 7% to 10% (v/v) 1,6-hexanediol, 0.002% (w/v) $NaN_3$, 0.0005% (w/v) 2,6-di-t-butyl-β-cresol, and 150 mM NaCl. The screening of the crystallization was carried out by a hanging drop vapor diffusion method at 15° C. The crystals appeared approximately 2 weeks later, and grew to not less than 50×50×50 µm³ within approximately 1 month to 2 months. The crystals were soaked for 1 hour in a reservoir solution to which 10% (w/v) glycerol had been added, and was rapidly cooled in a cooling nitrogen gas while being placed on a cryoloop. With use of BL32xU of SPring-8 including MX225HE CCD detector (Reference Literature 10, Reference Literature 11) or BL41XU of SPring-8 including MX225HE CCD detector, X-ray diffraction data on the crystals was collected in 100 K cryostream. The SAD data on the crystals was collected at a wavelength of 0.9793 Å. Approximately 240 diffraction images were collected from each crystal, and image data was processed by HKL-2000 (Reference Literature 12) or XDS (Reference Literature 13). The crystals of the claudin-4-C-CPE complex exhibited the following: space group: C2, lattice constant: a=126.9 Å, b=46.5 Å, c=160.4 Å, β=111.4°. The crystals of the T4L-claudin-4-C-CPE complex exhibited the following: space group: $P4_3$, lattice constant: a=b=105.9 Å, c=224.3 Å.

Example 10

Figure 21:
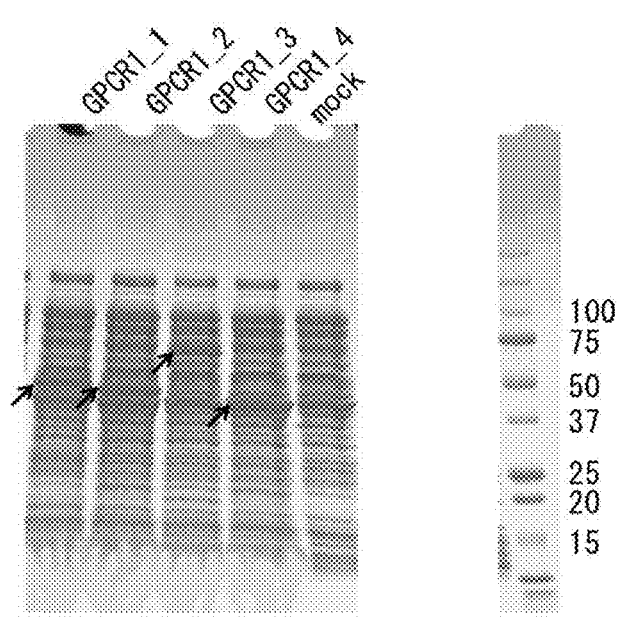
FIG. 21 is a view illustrating yet another example of the present invention.

Example 10 demonstrates that kinds of membrane proteins other than the membrane protein described above are applicable (FIG. 21). The reaction solution contained (i) porcine brain lipid at a final concentration of 4.3 mg/ml and (ii) a detergent (1% Brij-78). The reaction solution was fractionated by centrifugation (100,000 g, 15 minutes) and analyzed with SDS-PAGE. The arrows in FIG. 21 indicate the bands of GPCR1_1 (54.5 kDa), GPCR1_2 (47.7 kDa), GPCR1_3 (64.7 kDa), and GPCR1_4 (45.5 kDa), which are transmembrane receptors.

Example 11

(Comparison 1 with Conventional Techniques)

Example 11 discusses comparative experiments with the method disclosed in Patent Literature 6 (hereinafter referred to as "liposome method") and with the method disclosed in Patent Literature 2 (hereinafter referred to as "detergent method").

Comparative experiments were conducted so as to synthesize claudin-4 by the liposome method and by the method of an embodiment of the present invention, which claudin-4 had been obtained by fusing a modified native polyhistidine tag (N11, MKDHLIHNHHKHEHAHAEH) affinity tag to N-terminus. According to the liposome method, lipid and a detergent are added to a reaction solution for cell-free protein synthesis, as in the case of the embodiment of the present invention. However, while the membrane protein is being synthesized, a detergent concentration is lowered by a dialysis method or the like, so that lipid-detergent mixed micelles are stably formed into a lipid membrane (liposome). While the membrane protein is being synthesized, the membrane protein is inserted into the lipid bilayer membrane environment of the liposome, and the membrane protein is collected as a precipitate through centrifugation or the like. Then, through a fractionating step by density gradient centrifugation and a solubilizing step, purification is carried out. Meanwhile, according to an embodiment of the present invention, in a case where a synthesized membrane protein is enclosed in lipid-detergent mixed micelle. Then, in a case where centrifugation is carried out, the lipid-detergent mixed micelle is collected as a supernatant and then purified. It is therefore possible to prevent loss of the membrane protein, which loss occurs in a gradient density fractionation step and a solubilizing step. The difference in steps between the liposome method and the method in accordance with an embodiment of the present invention is illustrated in FIG. 1.

According to the liposome method, liposome containing claudin-4 was purified by a glycerol gradient density fractionation method (lane 4 and lane 5 in (b) of FIG. 4). After the liposome was solubilized by 3 DDM, a synthesized product was purified by a tag (metal) affinity method. According to the method in accordance with an embodiment of the present invention, lipid-detergent mixed micelle containing claudin-4 was directly subjected to tag purification. As illustrated in (b) of FIG. 4, the production level of the liposome method was equivalent to that of the method in accordance with an embodiment of the present invention (lane 2 and lane 10 in (b) of FIG. 4). However, the solubilization efficiency by P DDM is low, so that most of the produced claudin-4 was lost in the gradient density fractionation step and the solubilizing step (lane 6 in (b) of FIG. 4). In contrast, according to the method in accordance with an embodiment of the present invention, it is unnecessary to carry out a gradient density fractionation step or a solubilizing step (lane 11 in (b) of FIG. 4). Therefore, in terms of the final yield of claudin-4 purified by tag affinity, which final yield is measured with respect to 1 mL of a cell-free synthesized solution, the following remarkable difference was observed: 0.11 mg according to the liposome method, and 0.38 mg according to the method in accordance with an embodiment of the present invention (lane 8 and lane 14 in (b) of FIG. 4). Furthermore, with use of a claudin-4 sample produced by the method in accordance with an embodiment of the present invention, it was possible to efficiently obtain a monoclonal antibody recognizing the tertiary structure of the claudin-4.

(Comparison 2 with Conventional Techniques)

With use of lipid, such as GalCer, identified in Example 1, GlcT was produced by the liposome method. In comparison with other lipids, the sample produced in the presence of GalCer (5%), cholesterol (5%), and egg PC (90%) exhibited a dramatically increased production level and a remarkably increased specific activity ((d) and (e) of FIG. 2). Because GalCer was binding strongly even after the solubilizing step of the liposome method, it was found that GalCer is one of the lipids which specifically bind to GlcT. Meanwhile, in a case where a porcine brain lipid mixture was used, a specificity approximately 2.7 times higher was observed. These results indicate that while one or more unknown lipids binding to GlcT presumably exist other than GalCer, such unknown lipid(s) were dissociated in the solubilizing step due to bindings which are weaker than that of GalCer. In addition, GlcT produced by the liposome method with use of the porcine brain lipid mixture exhibited a solubilization efficiency which was markedly low in the case of a mild detergent such as DDM ((f) of FIG. 2). This is because GlcT is embedded in sphingolipid such as GalCer and lipid microdomain (detergent-resistant domain, DRM) formed by cholesterol, which are contained in the porcine brain lipid mixture. DRM is difficult to be dissolved with a mild detergent, and can therefore be said to be unsuited for production of membrane proteins which are expressed while being embedded in DRM. Note that DRM is considered as not only a problem specific to the liposome method, but also a common problem for all of the membrane protein synthesis methods, typified by the conventional techniques, in which a solubilizing step is necessary.

Figure 10:
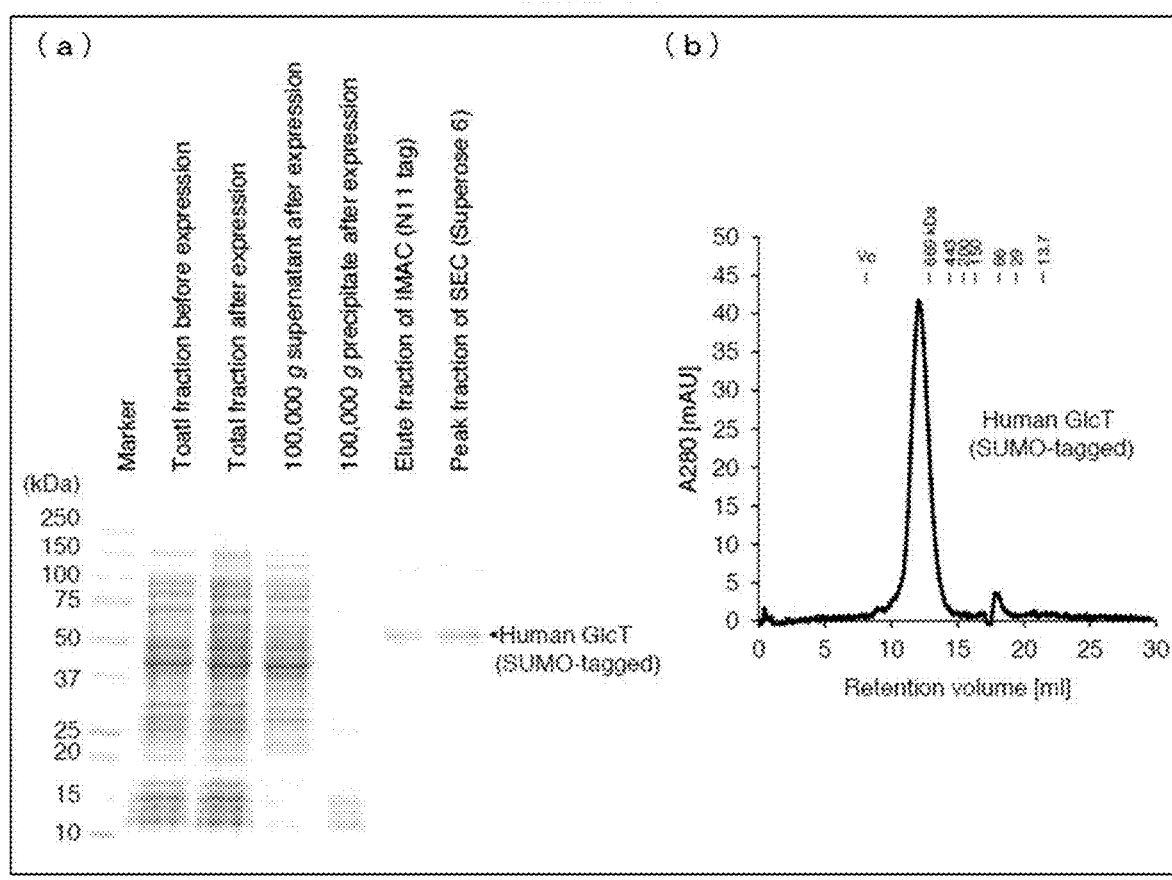
FIG. 10 is a view illustrating purification of human GlcT with use of the present invention. (a) of FIG. 10 shows purification of human GlcT prepared under conditions of 1% digitonin and porcine brain polar lipid extract by use of the present invention. A specimen in each purifying step was analyzed by SDS-PAGE and CBB staining. (b) of FIG. 10 shows an elution profile, on a gel filtration column (Superose6 increase 10/300 (GE)), of final purified specimen of human GlcT prepared by use of the present invention.

Therefore, in accordance with an embodiment of the present invention, GlcT was produced with use of a porcine brain lipid mixture. According to an embodiment of the present invention, GlcT having a yield higher in comparison with the case of the liposome method ((a) of FIG. 10), and it was possible to purify homogeneous GlcT after a chromatography step was carried out several times ((b) of FIG. 10). This indicates that the present invention, which requires neither a gradient density fractionation step nor a solubilizing step, has such an advantage as (i) preventing loss in yield which loss occurs in a gradient density fractionation step and a solubilizing step and (ii) allowing for production of GlcT without encountering the problem of DRM. In addition, suitable lipid can be selected for (bound to) a target membrane protein with use of a lipid mixture containing unknown lipids. Furthermore, the method in accordance with an embodiment of the present invention has an advantage that even in a case where the synthesized target membrane protein is directly purified, GlcT can be produced without causing the dissociation of lipid binding to the membrane protein with a weak binding force.

(Comparison 3 with Conventional Techniques)

According to a detergent method, an *E. coli* reaction solution for cell-free protein synthesis contains a detergent, but does not contain lipid. The synthesized membrane protein is collected as proteomicelle in a supernatant of a centrifugate. In a case where the detergent method is employed, the protein synthetic yield appears to be high. However, in comparison with the liposome method and with the method in accordance with an embodiment of the present invention, structural uniformity and stability of synthesized proteins are inferior in most cases.

Figure 11:
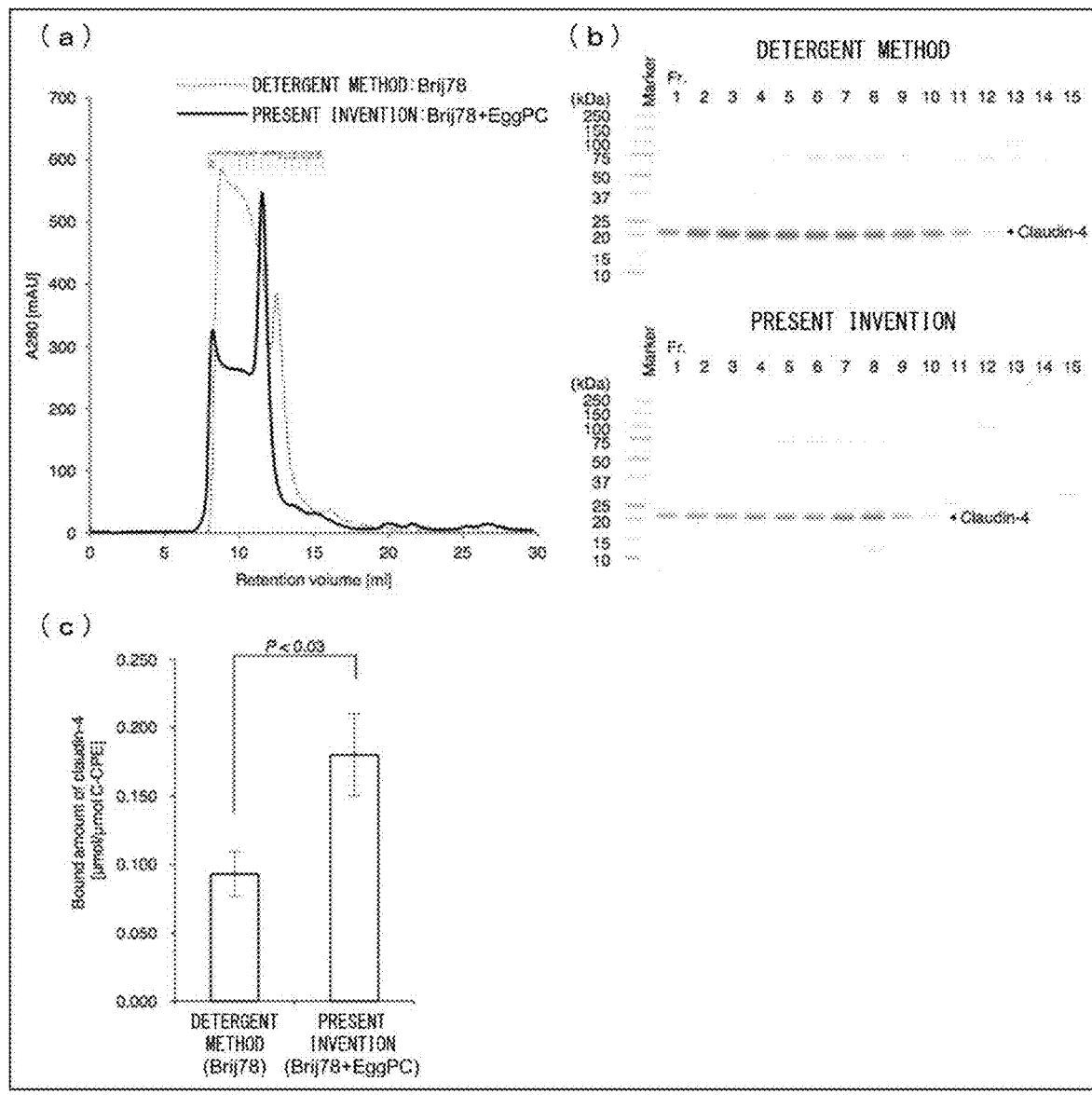
FIG. 11 is a view showing comparison between human claudin-4 synthesized by the conventional technique (detergent method) and by the method in accordance with an embodiment of the present invention.

A comparative experiment of synthesizing human claudin-4 was conducted such that 1% Brij-78 was used for the detergent method, and 1% Brij-78 and 0.67% egg PC were used for the method in accordance with an embodiment of the present invention ((a) through (c) of FIG. 11). The dotted line and the solid line in (a) of FIG. 11 indicate SEC elution profiles of proteins synthesized by the detergent method and by the method in accordance with an embodiment of the present invention, respectively. (b) of FIG. 11 shows SDS-PAGE images of CBB-stained SEC fractions. (c) of FIG. 11 shows the results of analyzing the binding of GST tag-added C-CPE and C-CPE by a pull-down assay in which SEC peak fraction was used. These results indicate that with the method in accordance with an embodiment of the present invention, it is possible to synthesize human claudin-4 having a correct structure in an amount larger in comparison with the case of the detergent method.

Example 12

Figure 7:
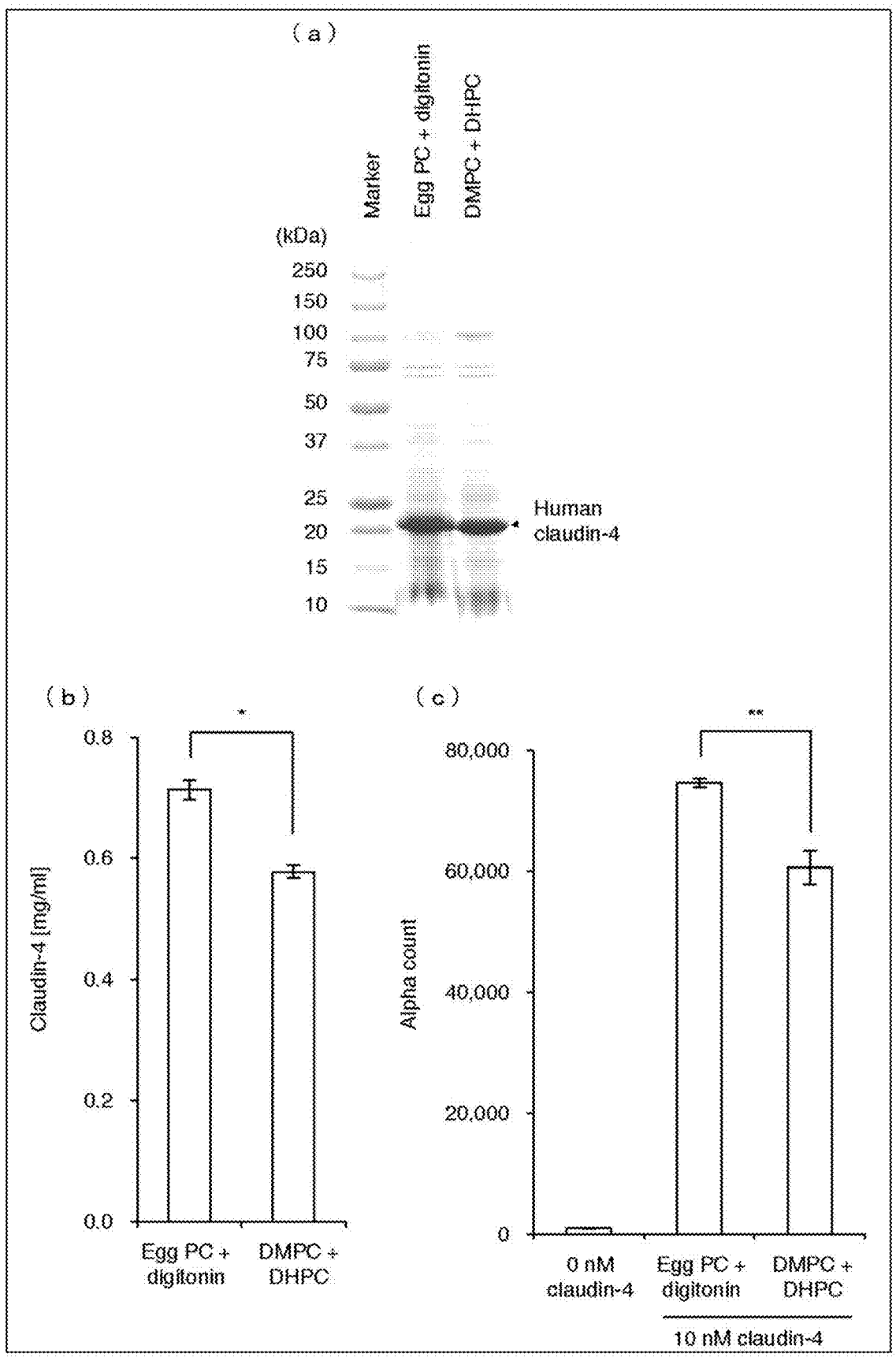
FIG. 7 shows that a combination of DMPC (2-dimyristoyl-sn-glycero-3-phosphocholine) and DHPC (2-diheptanoyl-sn-glycero-3-phosphocholine), which combination is typically used in a prepared bicelle addition method, can be applied to the present invention. (a) of FIG. 7 illustrates SDS-PAGE images showing IMAC elution of human claudin-4 which was produced in the presence of 10 mg/mL digitonin and 6.7 mg/mL egg PC or in the presence of 9.5 mg/mL DHPC and 6.7 mg/mL DMPC. (b) of FIG. 7 illustrates human claudin-4 concentrations estimated by desintometry analysis of (a) of FIG. 7.

Example 12 demonstrates that a combination of DMPC (2-dimyristoyl-sn-glycero-3-phosphocholine) and DHPC (2-diheptanoyl-sn-glycero-3-phosphocholine), which combination is typically used in a prepared bicelle addition method, can be applied to the present invention (FIG. 7). (a) of FIG. 7 illustrates SDS-PAGE images after (i) producing human claudin-4 in the presence of 10 mg/mL digitonin and 6.7 mg/mL egg PC or in the presence of 9.5 mg/mL DHPC and 6.7 mg/mL DMPC and (ii) subjecting the human claudin-4 to IMAC elution. (b) of FIG. 7 shows human claudin-4 concentrations estimated based on the analysis of the concentrations of (a) of FIG. 7. These results indicate that the combination of DMPC and DHPC is applicable to the present invention. However, the synthetic yield is decreased in comparison with the combination of the egg PC and digitonin. This is presumably because DMPC is not the most suitable lipid for synthesis of human claudin-4. In addition, these results indicate the limitation on the kinds of selectable lipids. Furthermore, these results indicate the technical limitation, on membrane protein synthesis, of the prepared bicelle addition method in which it is necessary to make adjustments with (i) a q value or a q value and a $C_L$ value.

Example 13

In Example 13, a comparison was made between (i) a prepared bicelle addition method in which a membrane protein was synthesized by adding a bicelle formed in advance to an *E. coli* reaction solution for cell-free protein synthesis while the q value was set to 0.5 as in Non-Patent Literature 2 and Non-Patent Literature 3, with use of the combination of DMPC (2-dimyristoyl-sn-glycero-3-phosphocholine) and DHPC (2-diheptanoyl-sn-glycero-3-phosphocholine) and (ii) the method in accordance with an embodiment of the present invention in which a membrane protein was synthesized at the same DMPC/DHPC concentrations. In the example shown in (a) of FIG. 22, a bicelle prepared in advance according to the method ordinarily used was added to the reaction solution, and the resulting mixture was subjected to synthesis reaction for 4 hours. This synthesized a channel A. The reaction solution after the synthesis was fractionated by centrifugation (100,000 g, 15 minutes). Then, the supernatant fraction and the precipitate fraction were analyzed with SDS-PAGE. In the example shown in (b) of FIG. 22, the method in accordance with an embodiment of the present invention was used so that DMPC and DHPC were added to the reaction solution without forming a bicelle in advance, and then the resulting mixture was subjected to synthesis reaction for 4 hours. This synthesized a channel A. The reaction solution after the synthesis was fractionated by centrifugation (100,000 g, 15 minutes). Then, the supernatant fraction and the precipitate fraction were analyzed with SDS-PAGE. The quantification of the ratio between the bands of the channels A detected in the supernatant fractions revealed that the yield in accordance with an embodiment of the present invention ((b) of FIG. 22) was approximately 20% higher in comparison with the yield of the prepared bicelle addition method ((a) of FIG. 22).

Meanwhile, there are reports concerning bicelles prepared with use of various q values and various combinations of q values and $C_L$ values. However, a membrane protein synthesis method in which a bicelle is added to a cell-free protein synthesis system is disclosed only in Non-Patent Literature 2 and Non-Patent Literature 3, in each of which the bicelle was prepared while the q value was set to 0.5. Non-Patent Literature ("Characterization of the Morphology of Fast-Tumbling Bicelles with Varying Composition") reports that in a case where a q value is 0.5, the shape of a bicelle is stable independently of a temperature and a total lipid concentration.

Meanwhile, according to the method in accordance with an embodiment of the present invention, it is unnecessary to consider any of the following when combining lipid and a detergent: (i) the chain lengths of a lipid and a detergent, (ii) a q value, and (iii) a q value and a $C_L$ value. However, for the sake of clear contrast with Non-Patent Literature 2 and with Non-Patent Literature 3, DMPC and DHPC which cover a wide range of concentrations are added (synthesis reaction for 4 hours, centrifugation (100,000 g, 15 minutes)), and the resulting membrane protein yields in SDS-PAGE were compared ((c) of FIG. 22 and (b) of FIG. 22). The results confirmed that there exist DMPC/DHPC concentration conditions under which the yield of membrane proteins considerably increases (4th lane from the left in (c) of FIG. 22: increased by 62%). These results indicate the possibility that according to the prepared bicelle addition method, the synthesis of membrane proteins is forced under conditions (q value: 0.5) which are not necessarily the most suitable, due to the restriction on the q value or on the q value and a $C_L$ value. According to the method in accordance with an embodiment of the present invention, in contrast, there are no restrictions unlike the prepared bicelle addition method. This advantageously allows membrane proteins to be synthesized under the most suitable conditions selected from a wide range of conditions for lipids and detergents.

Example 14

It has been reported that small-sized bicelles have a property of becoming isotropic with respect to a magnetic field so as to allow high-resolution measurement to be carried out by solution NMR, and that small bicelles (hereinafter referred to as "isotropic bicelle") are therefore suited for the structural analysis of membrane proteins by NMR (Non-Patent Literature "Isotropic solutions of phospholipid bicelles: A new membrane mimetic for high-resolution NMR studies of polypeptides"), (Non-Patent Literature "Detailed Description of the Conformation and Location of Membrane-Bound Erythromycin A Using Isotropic Bicelles"). Although the definition of isotropic bicelle varies depending on literature, it has been reported that isotropic bicelles are formed with a q value falling within a range of 0.05 to 0.5 (Non-Patent Literature (Structural Evaluation of Phospholipid Bicelles for Solution-State Studies of Membrane-Associated Biomolecules"). In addition, isotropic bicelles having a q value of 0.25 to 0.5 are most used for analysis by solution NMR (Non-Patent Literature "Choosing membrane mimetics for NMR structural studies of transmembrane proteins", Non-Patent Literature "Recent Advances in the Application of Solution NMR Spectroscopy to Multi-Span Integral Membrane Proteins", and Non-Patent Literature "Solution NMR of membrane proteins in bilayer mimics-small is beautiful, but sometimes bigger is better").

Figure 23:
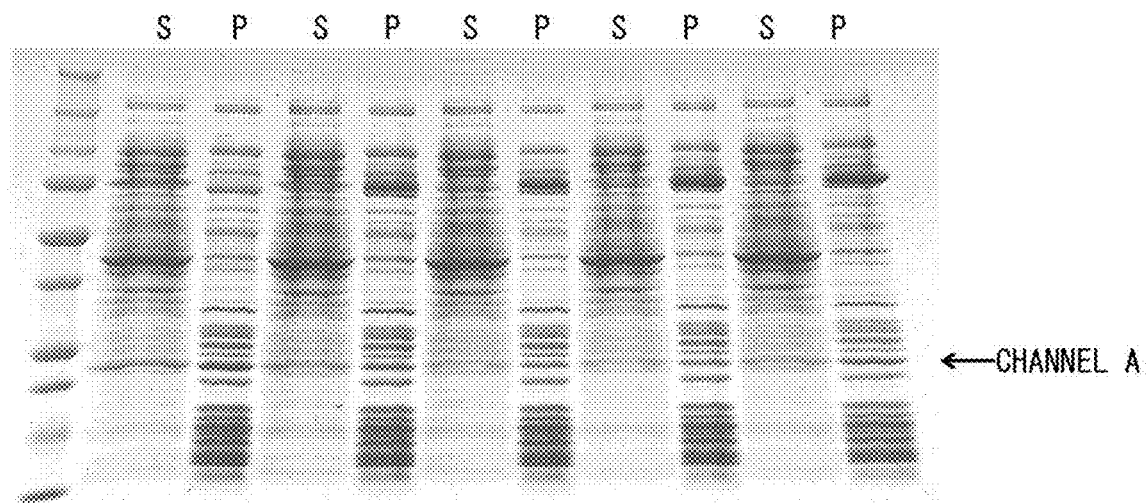
FIG. 23 is a view illustrating yet another example of the present invention.

Meanwhile, it is reported that in the case of isotropic bicelles having a q value of 0.5, when a $C_L$ value is not more than 1%, all of short-chain lipids are dissociated so as to cause a bicelle to collapse, so that a lipid vesicle composed only of long-chain lipids is formed (Patent Literature "Bicelles in structure-function studies of membrane-associated proteins"). Therefore, Example 14 demonstrates that a membrane protein can be produced by the method in accordance with an embodiment of the present invention, under conditions which prevent the formation of a bicelle in which (i) a molar ratio between DMPC and DHPC (referred to as "q value" for a bicelle) is not more than 0.3, which is even lower than 0.5 and (ii) a $C_L$ value is 1%. Channels A were synthesized by the experiment method described in Example 13 under the following conditions: the q values were 0.05, 0.1, 0.2, 0.25, and 0.3, and the $C_L$ value was 1%. The results confirmed that a channel A can be produced under all of the DMPC/DHPC conditions (FIG. 23). These results indicate that the method in accordance with an embodiment of the present invention is different from the prepared bicelle addition method.

Example 15

Figure 24:
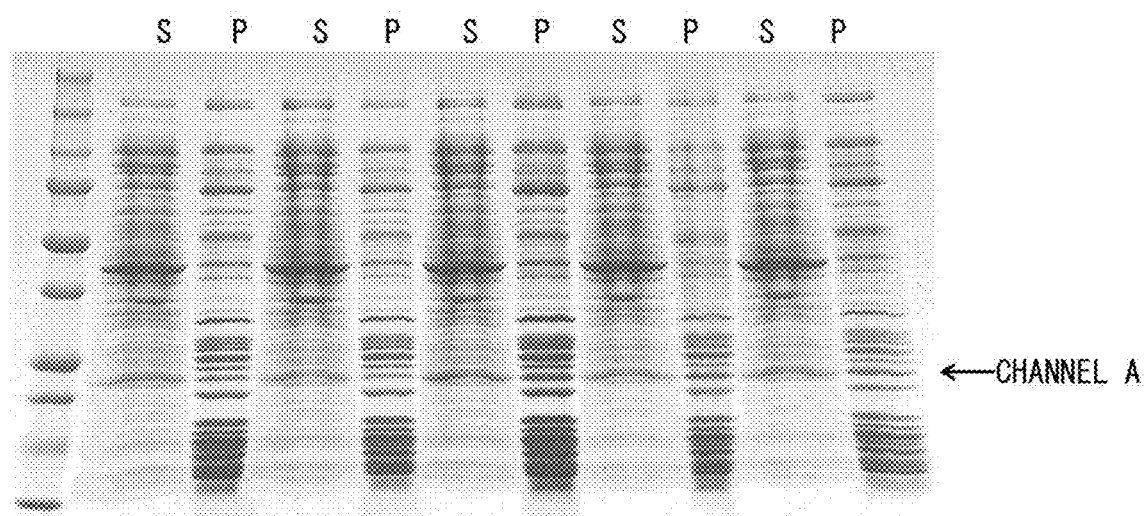
FIG. 24 is a view illustrating yet another example of the present invention.

Example 15 demonstrates that a membrane protein can be produced by the method in accordance with an embodiment of the present invention in a case where the molar ratio between DMPC and DHPC is lower than the lower limit value (q value of 0.05) at which an isotropic bicelle is formed. Channels A were synthesized by the experiment method described in Example 13. The results confirmed that a channel A can be produced under all of the DMPC/DHPC conditions (FIG. 24).

[Recap]

Note that the disclosures in Examples are merely illustrative of methods enabling synthesis of a membrane protein in accordance with an embodiment of the present invention. It is possible to make various changes to the kinds and amounts of lipids and detergents used for reactions in the methods, and the changes can be conceived by a person skilled in the art in view of the disclosures in the present application.

Therefore, in addition to what is claimed in the Claims, an embodiment of another aspect of the present invention is characterized by including: "(a) a step of selecting a reaction condition under which a membrane protein can be collected in a soluble fraction in a cell-free protein synthesis system including (i) a polypeptide encoding a membrane protein, (ii) a lipid, and (iii) a detergent, where the membrane protein is being soluble due to being enclosed in a lipid-detergent mixed micelle smaller than a liposome, and is synthesized under the reaction condition selected above; and (b) a step of purifying the membrane protein collected from the soluble fraction."

According to the embodiment, the kinds of lipids and detergents suited for target membrane proteins can be selected. In addition, the lipids and the detergents can be added at most suitable concentrations. This allows a membrane protein, which is collected in a soluble fraction, to be obtained as a homogeneous molecule which is enclosed in a lipid-detergent mixed proteomicelle and which has a correct tertiary structure. This membrane protein, as an immunogen having high purity and high quality, can be easily utilized by a known method so as to obtain an antibody. It is also possible to obtain a membrane protein crystal having high quality. Furthermore, membrane protein after purification can be reconstructed into a large lipid bilayer such as a liposome, and the functions of the membrane protein can be analyzed in an environment similar to that of a living cell. This is useful in the industrial fields of, for example, (i) screening of novel pharmaceutical compounds, (ii) analysis of biofunctions, and (iii) development of diagnostic apparatuses.

REFERENCES

1: Opekarova, M. & Tanner, W. Specific lipid requirements of membrane proteins—a putative bottleneck in heterologous expression. Biochim. Biophys. Acta 1610, 11-22 (2003).
2: Hanson, M. A. et al. A specific cholesterol binding site is established by the 2.8 Å structure of the human 12-adrenergic receptor. Structure 16, 897-905 (2008).
3: Sonoda, Y. et al. Benchmarking membrane protein detergent stability for improving throughput of high-resolution X-ray structures. Structure 19, 17-25 (2011).
4: Ichikawa, S., Sakiyama, H., Suzuki, G., Hidari, K. I. & Hirabayashi, Y. Expression cloning of a cDNA for human ceramide glucosyltransferase that catalyzes the first glycosylation step of glycosphingolipid synthesis. Proc. Natl. Acad. Sci. USA 93, 4638-4643 (1996).
5: Komori, H., Ichikawa, S., Hirabayashi, Y. & Ito, M. Regulation of UDP-glucose: ceramide glucosyltransferase-1 by ceramide. FEBS Lett. 475, 247-250 (2000).
6: Tomita, T. Molecular mechanism of intramembrane proteolysis by γ-secretase. J. Biochem. 156, 195-201 (2014).
7: Watanabe, N. et al. Pen-2 is incorporated into the γ-secretase complex through binding to transmembrane domain 4 of presenilin 1. J. Biol. Chem. 280, 41967-41975 (2005).
8: Takeo, K. et al. Allosteric regulation of γ-secretase activity by a phenylimidazole-type γ-secretase modulator. Proc. Natl. Acad. Sci. USA (2014).
9: Sonoda, N. et al. *Clostridium perfringens* enterotoxin fragment removes specific claudins from tight junction strands: Evidence for direct involvement of claudins in tight junction barrier. J. Cell Biol. 147, 195-204 (1999).
10: Hirata, K. et al. New micro-beam beamline at SPring-8, targeting at protein micro-crystallography. AIP Conf. Proc. 1234, 901-904 (2010).
11: Hirata, K. et al. Achievement of protein micro-crystallography at SPring-8 beamline BL32XU. J. Phys. Conf. Ser. 425, 012002 (2013).
12: Otwinowski, Z. & Minor, W. Processing of X-ray Diffraction Data Collected in Oscillation Mode. Methods Enzymol., 307-326 (1997).
13: Kabsch, W. XDS. Acta Crystallogr. D Biol. Crystallogr. 66, 125-132 (2010).
14: Emsley, P., Lohkamp, B., Scott, W. G. & Cowtan, K. Features and development of Coot. Acta Crystallogr. D Biol. Crystallogr. 66, 486-501 (2010).

INDUSTRIAL APPLICABILITY

The present invention allows a membrane protein having excellent quality to be obtained with a high yield. The present invention can therefore be used in, for example, the pharmaceutical fields such as drug design, antibody drug, and drug search.

The invention claimed is:

1. A method of producing a membrane protein with use of a cell-free protein synthesis system, comprising:
   a step (a) of adding a template nucleic acid, a lipid, and a detergent to a reaction solution for cell-free protein synthesis, which template nucleic acid encodes the membrane protein; and
   a step (b) of synthesizing the membrane protein by incubating the mixture resulted in the step (a) while the concentration of the detergent in the reaction solution is maintained at a concentration equal to or higher than the critical micelle concentration of the detergent, the detergent and the lipid being added to the reaction solution without being combined in advance which preparation causes a lipid membrane made of the detergent and/or the lipid to be stably formed, and the step (b) being started in a state in which, although lipid-detergent mixed micelles are formed, the lipid-detergent mixed micelles are not fused with each other to grow into a lipid membrane which is stably formed.

2. The method as set forth in claim 1, further comprising:

a step (c) of collecting, from a supernatant of a centrifugate or from a purified eluate, a lipid-detergent mixed proteomicelle in which the lipid and the detergent are bound to the membrane protein.

\* \* \* \* \*

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial sequence
<220> FEATURE:
<223> OTHER INFORMATION: synthetic

<400> SEQUENCE: 1

Gly Gly Val Val Ile Ala Thr Val Lys Asp Arg Asp Arg Asp Arg
1               5                   10                  15

<210> SEQ ID NO 2
<211> LENGTH: 7
<212> TYPE: PRT
<213> ORGANISM: Artificial sequence
<220> FEATURE:
<223> OTHER INFORMATION: synthetic

<400> SEQUENCE: 2

Gly Ser Ser Gly Ser Ser Gly
1               5
```